(12) United States Patent
Studer et al.

(10) Patent No.: US 12,383,770 B2
(45) Date of Patent: Aug. 12, 2025

(54) VENTILATION APPARATUS AND MASK

(71) Applicant: AVIATION WORKS LTD, London (GB)

(72) Inventors: Marc Studer, Lucerne (CH); Gunnar Jansen, Bulach (CH); Tim Wakeford, London (GB); Rob Boyle, London (GB)

(73) Assignee: AVIATION WORKS LTD, London (GB)

( * ) Notice: Subject to any disclaimer, the term of this patent is extended or adjusted under 35 U.S.C. 154(b) by 1120 days.

(21) Appl. No.: 17/261,106

(22) PCT Filed: Jul. 19, 2019

(86) PCT No.: PCT/EP2019/069538
§ 371 (c)(1),
(2) Date: Jan. 18, 2021

(87) PCT Pub. No.: WO2020/016422
PCT Pub. Date: Jan. 23, 2020

(65) Prior Publication Data
US 2021/0330996 A1   Oct. 28, 2021

(30) Foreign Application Priority Data
Jul. 19, 2018   (EP) ..................................... 18184568

(51) Int. Cl.
*A62B 7/14* (2006.01)
*A61M 16/00* (2006.01)
(Continued)

(52) U.S. Cl.
CPC ........... *A62B 7/14* (2013.01); *A61M 16/0057* (2013.01); *A61M 16/06* (2013.01);
(Continued)

(58) Field of Classification Search
CPC .. A62B 7/14; A62B 7/00; A62B 9/003; A62B 9/02; A62B 19/00; A62B 23/00;
(Continued)

(56) References Cited

U.S. PATENT DOCUMENTS 3,489,144 A * 1/1970 Dibelius .................. A62B 7/10
128/205.12
4,233,842 A * 11/1980 Raemer ..................... G01F 1/74
73/861.04
(Continued)

FOREIGN PATENT DOCUMENTS

| CN | 2555042 Y | 6/2003 |
|---|---|---|
| CN | 101511432 A | 8/2009 |

(Continued)

OTHER PUBLICATIONS

International Search Report and Written Opinion for PCT Application No. PCT/EP2019/069538 Mailed Sep. 24, 2019; 14 Pages.

*Primary Examiner* — Tu A Vo
*Assistant Examiner* — Kelsey E Baller
(74) *Attorney, Agent, or Firm* — Fletcher Yoder, P.C.

(57) ABSTRACT

There is provided an apparatus for preparing a ventilation gas mixture that comprises a gas mixing device, a first gas feed arranged to supply a first gas to the gas mixing device, an air inlet configured to receive exhaled air from a person, a gas reservoir arranged to store carbon dioxide from the air received in the air inlet and further arranged to supply the stored carbon dioxide to the gas mixing device via a second gas feed, wherein the gas mixing device is arranged to combine the first gas with the carbon dioxide in order to prepare the ventilation gas mixture.

36 Claims, 14 Drawing Sheets

(51) Int. Cl.
  *A61M 16/06* (2006.01)
  *A61M 16/10* (2006.01)
  *A61M 16/12* (2006.01)
  *A61M 16/20* (2006.01)
  *A61M 16/22* (2006.01)
  *A62B 7/00* (2006.01)
  *A62B 9/00* (2006.01)
  *A62B 9/02* (2006.01)
  *A62B 19/00* (2006.01)
  *A62B 23/00* (2006.01)

(52) U.S. Cl.
  CPC ...... *A61M 16/1005* (2014.02); *A61M 16/105* (2013.01); *A61M 16/1075* (2013.01); *A61M 16/125* (2014.02); *A61M 16/208* (2013.01); *A61M 16/22* (2013.01); *A62B 7/00* (2013.01); *A62B 9/003* (2013.01); *A62B 9/02* (2013.01); *A62B 19/00* (2013.01); *A62B 23/00* (2013.01); *A61M 2202/0266* (2013.01); *A61M 2205/7536* (2013.01)

(58) Field of Classification Search
  CPC .............. A61M 16/0057; A61M 16/06; A61M 16/1005; A61M 16/105; A61M 16/1075; A61M 16/125; A61M 16/208; A61M 16/22; A61M 16/209; A61M 16/122; A61M 2016/1025; A61M 2202/0208; A61M 2202/0225; A61M 2202/0266; A61M 2205/3341; A61M 2205/7536; B64D 2231/02; B64D 2231/025
  See application file for complete search history.

(56) References Cited

U.S. PATENT DOCUMENTS

| | | | |
|---|---|---|---|
| 5,520,169 A * | 5/1996 | Georgieff | A61M 16/101 |
| | | | 128/203.29 |
| 5,957,129 A | 9/1999 | Tham et al. | |
| 6,041,777 A * | 3/2000 | Faithfull | A61M 16/0054 |
| | | | 128/200.24 |
| 6,213,120 B1 * | 4/2001 | Block | A61M 16/0075 |
| | | | 128/204.23 |
| 6,471,747 B1 | 10/2002 | Venkatesh et al. | |
| 6,895,961 B1 | 5/2005 | Todorov | |
| 7,497,215 B1 * | 3/2009 | Nguyen | A61M 16/0057 |
| | | | 128/205.27 |
| 9,770,569 B2 * | 9/2017 | Heesch | A61M 16/18 |
| 10,226,591 B1 * | 3/2019 | Tarler | A61M 16/022 |
| 2005/0113709 A1 * | 5/2005 | Millet | A61B 5/4818 |
| | | | 600/529 |
| 2007/0017516 A1 | 1/2007 | Schmidt | |
| 2007/0163591 A1 * | 7/2007 | Ross | A62B 21/00 |
| | | | 128/205.12 |
| 2008/0314386 A1 | 12/2008 | Myklebust et al. | |
| 2012/0017908 A1 * | 1/2012 | Muellner | A61M 16/12 |
| | | | 128/205.12 |
| 2016/0213879 A1 * | 7/2016 | Parthasarathy | A61M 16/208 |
| 2016/0355262 A1 | 12/2016 | Sharma | |
| 2018/0154191 A1 | 6/2018 | Studer | |
| 2019/0321576 A1 * | 10/2019 | Boulanger | A61M 16/12 |

FOREIGN PATENT DOCUMENTS

| | | |
|---|---|---|
| CN | 205634885 U | 10/2016 |
| CN | 107405510 A | 11/2017 |
| WO | 2008010021 A1 | 1/2008 |
| WO | 2016102450 A1 | 6/2016 |

* cited by examiner

VENTILATION APPARATUS AND MASK

FIELD OF THE INVENTION

The invention relates to an apparatus and a method for preparing a ventilation mixture and a ventilation mask for ventilation or respiratory support in such an apparatus. The invention also relates to the use of such an apparatus, ventilation mask and/or such a method for ventilating individuals with limited mobility or generally in the event of hyperventilation, or for ventilating individuals in aircraft, particularly in the event of loss of pressure, or to delay a critical oxygen-saturation during ventilation of individuals, particularly in hypoxia applications, or as a countermeasure for hypocapnia risks or to stabilise the blood pH level in individuals for the purpose of administering additional oxygen or for pre-oxygenation prior to intubation.

BACKGROUND

Each human body has its own typical oxygen saturation value, which varies according to age, situation and clinical picture. This value indicates the proportion of oxygen-charged haemoglobin in the blood, which in turn gives an indication of the efficiency with which breathing and oxygen transport is carried out in the body. Oxygen undersaturation is caused either by oxygen partial pressure in the environment which is too low for humans (for example at an altitude above 10'000 ft or 3048 m) and/or as a consequence of health disorders. On this basis, the treatment measures also vary. With regard to ventilation, a fundamental distinction is made between assisted ventilation and supervised (mandatory) ventilation. In this context, a ventilation device used for assisted ventilation serves purely as an auxiliary measure when spontaneous breathing is insufficient. The patient breathes unaided and controls the respiratory frequency. On the other hand, in the case of supervised ventilation the ventilation device replaces the body's endogenous respiratory function entirely. The concentration of oxygen in the artificially supplied air can be adjusted between a normal concentration of 21% up to 100% of the gas mixture according to needs. The percentage of oxygen breathed in is called the "fraction of inspired oxygen" (Fioxygen). It is known that a Fioxygen of more than 0.5 (corresponding to an oxygen percentage of 50% in the breathed air) administered for a prolonged period has a damaging effect. After all, oxygen is a powerful oxidising agent, which also oxidises other substances present in the blood besides haemoglobin. However, enzymes in the body reverse this oxidation process. On the other hand, if pure oxygen is introduced into a body for longer than a certain period of time, because of the stronger oxidation of haemoglobin and other proteins the "methaemoglobin reductase" is no longer able to correct this damage. After the body's endogenous antioxidising system is exhausted, the oxygen radicals released cause oxygen toxicity with symptoms becoming apparent in the central nervous system, the lungs and the eyes. Despite this, patients in life-threatening condition are still ventilated—even if only for briefperiods—with pure oxygen, i.e. with Fioxygen=1. Also in the case of preoxygenation, the prophylactic enrichment of the oxygen reservoir in the lungs before anaesthetic induction for example, the patient receives 100% pure oxygen in order to wash the nitrogen contained in the breathed air out of the respiratory tract. Pure oxygen is also used to ventilate crew and passengers in the event of a pressure drop in an aircraft cabin. In this case, the argument prevails that a large quantity of oxygen must be introduced as quickly as possible into body tissue which may already be suffering from insufficient supply. Possible side effects are therefore overridden and/or accepted.

However, the risks associated with ventilation are not attributable solely to the properties of oxygen. The carbon dioxide concentration in the (arterial) blood is also a critical factor. Breathing is controlled and regulated mainly via chemoreceptors or chemosensors which are sensitive to the carbon dioxide partial pressure (oxygen-sensitive or other receptors are less important in this process). The level of carbon dioxide in the blood is therefore a vegetative stimulus for regulating respiration. If the carbon dioxide content in the blood exceeds a characteristic threshold value, the respiratory drive is triggered. Conversely, with hyperventilation and resulting reduction of carbon dioxide partial pressure in the blood (hypocapnia), breathing rate is reduced reflectively.

In order to suppress the respiratory drive, inexperienced divers therefore often hyperventilate indiscriminately in order to expel carbon dioxide and immediately thereafter remain under water for longer. However, this entails with considerable risks, possibly to the point of losing consciousness and—in such a case—drowning (also called "freediving blackout"). As the endogenous carbon dioxide content falls, deficiency symptoms ranging in severity from unpleasant to life-threatening may manifest themselves, as will be described in detail later. The carbon dioxide-level lowering effect of hyperventilation is further reinforced if freedom of movement is limited. Because in this situation the muscles produce less endogenous carbon dioxide. The symptoms of carbon dioxide deficiency thus occur sooner and more intensely. This problem arises particularly in cases of depressurisation in an aircraft cabin, because the passengers' freedom of movement is necessarily limited. In such a situation, it is imperative to check the carbon dioxide-partial pressure during the ventilation process, for example by measuring the end-tidal carbon dioxide-partial pressure.

If the pressure in an aircraft cabin falls below a critical pressure value, the compartments above the seats open and the oxygen masks located in the cabin ceiling descend from their holders into the field of view of the aircraft occupants. Pure oxygen flows through the supply tube into the mask and finally reaches the nose and mouth when the person using the mask breathes in. For the supply to passengers, oxygen is either generated in chemical oxygen generators or stored in pressure cylinders, while the pilots in the cockpit are supplied with compressed gas oxygen through a separate system. The size of the oxygen supply on an aircraft depends on the aircraft's certification and its intended purpose, and on the routes it must fly. This calculation also takes into account whether the aircraft flies mostly over land or sea, or even whether it flies long distances over very high terrain and mountain ranges.

The time remaining for appropriate action in the event of a loss of pressure in an aircraft cabin is called the Time of Useful Consciousness (TUC) or Effective Performance Time (EPT). After this time, the body tissue and organs experience significant oxygen deficiency and the body becomes hypoxic. Below a certain level of oxygen saturation in the brain, an individual loses the ability to function and later loses consciousness. The TUC is specified for a flight level (level of uniform air pressure in the atmosphere, corresponding to a certain flying altitude in hundreds of feet) and becomes shorter with increasing flight altitude. The table shows TUC specifications for various flight levels.

| Flight level | TUC | Altitude in metres | Altitude in feet |
| --- | --- | --- | --- |
| FL 150 | 30 min | 4,572 | 15,000 |
| FL 180 | 20-30 min | 5,486 | 18,000 |
| FL 220 | 5-10 min | 6,705 | 22,000 |
| FL 250 | 3-6 min | 7,620 | 25,000 |
| FL 280 | 2.5-3 min | 8,534 | 28,000 |
| FL 300 | 1-3 min | 9,144 | 30,000 |
| FL 350 | 30-60 sec | 10,668 | 35,000 |
| FL 400 | 15-20 sec | 12,192 | 40,000 |
| FL 430 | 9-15 sec | 13,106 | 43,000 |
| ≥FL 500 | 6-9 sec | 15,240 | 50,000 |

The speed with which decompression takes place also affects the TUC. The faster the pressure loss takes place, the shorter the TUC is. Therefore, given the rapid onset of oxygen deficiency in the body, it is essential for survival that oxygen is supplied to the body as quickly as possible, which is why military pilots, who also fly higher than passenger aviation always have their oxygen masks ready for immediate use throughout the entire flight. There is no need for this in civilian air travel, since the cruising altitude of commercial aircraft is lower, specifically between FL 250 and FL 450, corresponding to a flight altitude of about 25'000 ft to 40'000 ft. As a rule, military and passenger aircraft also differ in that the differential pressure, that is to say the pressure difference between external and internal pressure is not the same in a military aircraft as in a passenger aircraft. In terms of the pressure conditions, a cabin in a passenger aircraft remains at about 8000 ft, for example, regardless of how high the aircraft is flying. In a military aircraft the cabin rises with a certain differential pressure parallel to the flight altitude. For example, the cabin altitude in an F/A-18 is about 20'000 ft when the aircraft is flying at 35'000 ft. Therefore, a military aircraft pilot is also obliged to wear an oxygen mask, typically as soon as the cabin altitude rises above 11'500 ft.

For commercial reasons, flight routes should ideally be flown over the shortest path between two airports. Nowadays, the ranges of modern commercial aircraft permit direct (inter)continental flights to destinations that until just a few years ago could not be reached without stopovers. But due to safety considerations, not all direct routes are open to aviation. Flying over high mountain ranges such as the Himalayas between India and Tibet, the Central Asian Hindu-Kush and the Andes in South America is only possible to a limited degree and under certain conditions. The decisive requirements are dictated by two distinct emergency situations: engine failure on the one hand and loss of cabin pressure on the other. In the first case, the danger resides in the loss of thrust due to the failure of one or more engines, forcing it to reduce altitude, since an aircraft with reduced thrust cannot maintain its cruising altitude. In such cases, escape routes enable the aircraft to execute a drift-down to the closest possible runway. The ICAO (International Civil Aviation Organization), the EASA (European Aviation Safety Agency), the JAA (Joint Aviation Authorities) and as well the FAA (U.S. Federal Aviation Administration) all prescribe that such emergency escape routes must satisfy a standard according to which a vertical clearance of at least 2'000 ft from the ground must be assured during the engine-out drift-down manoeuvre to the OEI (one-engine inoperable) service ceiling. and when level flight is re-established a vertical clearance of 1'000 feet above the ground and 2'000 feet above mountains within a specific lateral distance relative to the flight path. The provisions of the regulatory authorities differ with regard to the specific lateral track width for said obstacle clearance.

If emergency landings were caused by engine failure only, the sophisticated system of escape routes would allow for almost any direct flight routes, notwithstanding some minor deviations. But the second case of a possible emergency situation, that is to say loss of cabin pressure, represents a substantially more complicated set of problems. Besides the requirements mentioned above, the time factor is far more significant than in the case of engine failure. The number of potentially possible escape routes is reduced considerably, because on many such routes the required difference in altitude cannot be attained within a sufficiently short time. The standard procedure in the event of loss of cabin pressure is regulated by the ICAO. It provides that—after safely breathing through their own oxygen masks—pilots initiate a descent as quickly as possible to bring the aircraft to a safe altitude, i.e. to a level at which humans can breathe without additional oxygen supply. This must be accomplished within the bridging time predefined by the oxygen supply. Due to the limited space and weight capacity of aircraft, the oxygen reserve can be increased only at the cost of cargo or the maximum number of passengers. An improved ventilation of the aircraft passengers in case of cabin depressurization might also result in less oxygen having to be carried aboard the airplane, thus reducing the overall weight of the aircraft. Carrying a smaller quantity of oxygen also reduces the risk of fire which is associated with the fire accelerant effect of oxygen.

If the problem of artificial respiration did not exist, in many cases commercial aircraft would be able to fly to their destinations by a more direct route. If engine failure were the only limiting factor, correspondingly designed multi-engine aircraft with passengers aboard would be able to overfly any region, because the escape route system allows for a drift-down to the one-engine inoperable service ceiling on any route section. In practice however, the system of escape routes is designed so that the various escape paths satisfy the more restrictive of the two above-mentioned emergency situations—i.e. that of spontaneous cabin depressurization. An improved ventilation system for passengers in the event of cabin pressure loss which would require less oxygen to assure a sufficient supply would prolong the time available as determined by a conventional oxygen supply. Consequently, it may also not be necessary to implement safety precautions exceeding those prescribed for the case of engine failure. Without these additional limitations, itineraries might be flown over high-altitude terrain without detours and consequently thousands of tons of kerosene could be saved. The saving in fuel weight might enable either the loading capacity to be increased or the overall fuel consumption to be reduced, because the aircraft's weight is reduced by the deadweight of the excess fuel requirement. This would also contribute to environmental conservation. Moreover, flight times could be reduced considerably, offering not inconsiderable operational advantages besides enabling flights to more distant destinations.

The flight routes that are actively flown over extensive mountainous areas today involve substantial planning effort, besides actually carrying them out. In the event of major technical problems and malfunctions, it is primarily the pilots' responsibility to handle the emergency situation effectively, that is to take immediate decisions and implement the necessary steps. Since decisions in such situations are most often irreversible, the outcome of events is largely determined by humans who must react in these stress situations. Accordingly therefore, a significant risk of errors with possibly fatal consequences exists a priori. A less urgent time factor or a longer decision period in emergency situations would improve the quality of the decisions significantly and thus contribute substantially to safety.

In this context, in order to prolong the period remaining between the instant when the oxygen is made accessible to the air passengers and the instant when the aircraft has descended to a safe flight altitude corresponding to a high-density altitude in which humans can survive, to such a degree that in the event of pressure loss in the cabin the pilots have more time to take action and make decisions, WO 2016/102450 A1 suggests a gas mixture to be used for ventilation as needed, which includes a carbon dioxide-component that varies according pressure depending on the density altitude. This gas mixture may advantageously also find uses in other fields. However, conventional apparatuses and methods are not designed, or not adequately designed to prepare such a gas mixture.

It is therefore desirable to provide an apparatus and a method as well as a ventilation mask usable in the apparatus, which enables a ventilation gas mixture of variable composition to be prepared simply and provides for advantageous uses.

SUMMARY

According to a first aspect of the present invention there is provided an apparatus for preparing a ventilation gas mixture that comprises: a gas mixing device; a first gas feed arranged to supply a first gas to the gas mixing device; an air inlet configured to receive exhaled air from a person; a gas reservoir arranged to store carbon dioxide from air received in the air inlet and further arranged to supply the stored carbon dioxide to the gas mixing device via a second gas feed; wherein the gas mixing device is arranged to combine the first gas with the carbon dioxide in order to prepare the ventilation gas mixture.

As discussed, the duration of emergency oxygen supply in an aircraft is limited by the size of the emergency oxygen system, typically either a chemical or gaseous oxygen storage system. The size of the emergency oxygen system is primarily governed by size and weight restrictions of the aircraft. This effectively means that the size of the emergency oxygen system has a direct impact on the efficiency and fuel requirements of aircraft, and if aircraft were able to fly for longer at high altitudes (typically around 21,000 ft) after a depressurisation, then significant fuel could be saved.

The apparatus of the present invention advantageously provides a ventilation gas mixture, for example to a user such as passengers and aircraft crew, with relatively small quantities carbon dioxide added to the ventilation gas mixture in order to improve the body's use of the oxygen in the ambient air. The present invention achieves this by re-using exhaled carbon dioxide from the user's breath and mixing it with ambient air for form the ventilation gas mixture. Since the body is able to make more efficient use of the oxygen in the ventilation gas mixture, a lower quantity of emergency oxygen can be kept on board the aircraft. Thus, the overall size of the emergency oxygen system can be reduced.

The apparatus of the present invention provides users with a ventilation gas mixture which enables survival at high altitudes (for example, between 10,000 ft and 22,000 ft and above), for long periods of time, without adding a significant weight penalty to the aircraft. Advantageously, this enables significant fuel and efficiency savings for airlines to be made.

The gas reservoir may comprise a selectively sorbent material. The sorbent material may selectively store carbon dioxide. The air that is received in the air inlet and supplied to the gas reservoir comprises several components for example carbon dioxide, oxygen, and nitrogen. Using a selectively sorbent material helps ensure that only the component of air that is of interest, for example carbon dioxide, is captured and stored by the gas reservoir. This prevents the gas reservoir from storing components of the exhaled air that are not of interest.

The apparatus may further comprise a pump arranged to apply a pressure to the gas reservoir relative to the surroundings in order to controllably store carbon dioxide within the gas reservoir or controllably release the carbon dioxide from the gas reservoir.

In particular, the pump may be arranged to apply a positive pressure to the gas reservoir in order to store the carbon dioxide. The pump may be arranged to apply a negative pressure to the gas reservoir in order to release the carbon dioxide.

The apparatus may further comprise a moisture filter arranged to filter the air received from the air inlet before it is supplied to the gas reservoir. Thus, the moisture filter may be positioned in a flow path between the air inlet and the gas reservoir. This ensures that the exhaled air which enters the system through the air inlet has to pass through the moisture filter before it reaches the gas reservoir. The moisture filter is able to remove water molecules from the exhaled air before the air is supplied to the gas reservoir. This enables the gas reservoir to store relatively higher volumes of carbon dioxide than would be possible if the air had not had some water molecules removed first.

The apparatus may comprise a plurality of gas reservoirs. Each of the plurality of gas reservoirs may be arranged to store carbon dioxide from air received in the air inlet and may be further arranged to supply the stored carbon dioxide to the gas mixing device. Using more than one gas reservoir allows the apparatus to store a greater volume of carbon dioxide than would be possible with one gas reservoir.

The plurality of gas reservoirs may be fluidly coupled together. In other words, the plurality of gas reservoirs are in fluid communication with each other. This may be achieved by a gas feed line that is common to the plurality of gas reservoirs. Each of the plurality of gas reservoirs may be arranged to release its stored carbon dioxide into a common gas feed that is then used to supply all the collected carbon dioxide to the gas mixing device. Having one common gas feed line connected to a plurality of gas reservoirs simplifies the apparatus because the gas mixing device only requires one inlet for receiving the stored carbon dioxide from the plurality of gas reservoirs.

The plurality of gas reservoirs may comprise a primary gas reservoir and a secondary gas reservoir. The primary gas reservoir may be configured to carry out a capturing function in which the primary gas reservoir is configured to store carbon dioxide from air received in the air inlet. The secondary gas reservoir may be configured to carry out a supplying function in which the secondary gas reservoir is configured to supply stored carbon dioxide to the gas mixing device. The primary gas reservoir and secondary gas reservoir may be arranged to carry out their respective functions substantially simultaneously. This means that when one gas reservoir is storing carbon dioxide from the exhaled air, another gas reservoir is supplying its stored carbon dioxide to the gas mixing device, at the same time. This means that once the supplying gas reservoir has been emptied of carbon dioxide there will be another gas reservoir that has been filled with carbon dioxide, ready to supplying to the gas mixing device. The plurality of gas reservoirs therefore allows different reservoirs to be carrying out different functions to each other for example one gas reservoir is capturing and storing whilst another is releasing. However, in some cases, all the gas reservoirs may be carrying out the same function for example they may all be capturing and storing or they may all be releasing.

In some developments there may be more than two filters, for example four filters. In this case a first filter may be releasing, a second filter may be capturing and storing, a third filter may be preparing to release, and a fourth filter may be preparing to capture and store.

One or more valves may be associated with the plurality of gas reservoirs, the one or more valves arranged to switch the function of the primary gas reservoir to the supplying function and the function of the secondary gas reservoir to the capturing function. Thus, each gas reservoir in the plurality of gas reservoirs alternates between a capturing function and a supplying function. This ensures that there is a continuous supply of carbon dioxide gas to the gas mixing device. This helps ensure continuous production of the ventilation gas mixture.

In some cases, the plurality of gas reservoirs may be coupled together in series. Alternatively, the plurality of gas reservoirs may be coupled together in parallel.

The apparatus may further comprise a temperature control means arranged to adjust the temperature of the gas reservoir relative to the surroundings in order to controllably store carbon dioxide within the gas reservoir or controllably release the carbon dioxide from the gas reservoir. The temperature control means may be arranged to decrease the temperature of the gas reservoir relative to the surroundings in order to controllably store carbon dioxide within the gas reservoir. The temperature control means may further be arranged to increase the temperature of the gas reservoir relative to the surroundings in order to controllably release carbon dioxide from the gas reservoir. The apparatus can therefore be used to store and supply carbon dioxide using a combination of both pressure and temperature. Using both pressure and temperature results in more efficient storage of carbon dioxide in the gas reservoir from the exhaled air. However, the apparatus may store and supply carbon dioxide using either just pressure adjustments or just temperature adjustments.

The apparatus may further comprise a second gas reservoir arranged to store nitrogen from air received in the air inlet and further configured to exhaust nitrogen reduced air from an outlet in the second gas reservoir. The second gas reservoir therefore acts as a filtration device, specifically a nitrogen filtration device. The second gas reservoir may release the nitrogen stored in the second gas reservoir to the surroundings.

The outlet in the second gas reservoir may be arranged to supply the nitrogen reduced air to the gas mixing device. For some conditions, the carbon dioxide enriched air used to form the ventilation gas mixture will also have some of the nitrogen removed from the ambient air that the carbon dioxide is mixed with in order to further improve the effectiveness of the system.

The second gas reservoir may comprise a selectively sorbent material. The sorbent material may selectively store nitrogen. Since the air that is received in the air inlet and supplied to the second gas reservoir comprises several components, the selectively sorbent material helps ensure that only the component of air that is of interest, for example nitrogen, is captured and stored by the second gas reservoir. This prevents the second gas reservoir from storing components of the exhaled air that are not of interest.

A temperature control means may be arranged to adjust the temperature of the second gas reservoir relative to the surroundings in order to controllably store nitrogen within the second gas reservoir or controllably release the nitrogen from the second gas reservoir.

In particular, the temperature control means may be arranged to decrease the temperature of the second gas reservoir relative to the surroundings in order to controllably store nitrogen within the gas reservoir. Further, the temperature control means may be arranged to increase the temperature of the second gas reservoir relative to the surroundings in order to controllably release nitrogen from the second gas reservoir.

In some cases, the apparatus further comprises a pump arranged to apply a pressure to the second gas reservoir relative to the surroundings in order to controllably store nitrogen within the second gas reservoir or controllably release the nitrogen from the second gas reservoir. The pump may be arranged to apply a positive pressure to the second gas reservoir in order to store nitrogen. The pump may be further arranged to apply a negative pressure to the second gas reservoir in order to release the nitrogen. The apparatus can therefore be used to store and release nitrogen using a combination of both pressure and temperature adjustments. Using both pressure and temperature adjustments results in more efficient storage of nitrogen in the second gas reservoir from the ambient air. However, the apparatus may store and release nitrogen using either just pressure adjustments or just temperature adjustments.

In some cases, a ventilation mask may be configured to receive the ventilation gas mixture from the gas mixing device. The ventilation mask may therefore be coupled to and in fluid communication with the gas mixing device. Using a ventilation mask provides a comfortable and convenient means of supplying the ventilation gas mixture from the gas mixing device to a person. Coupling the gas mixing device to a ventilation mask allows the apparatus to be retrofitted to systems already comprising a ventilation mask.

In other cases, the gas reservoir and/or the second gas reservoir may form part of the ventilation mask. The gas mixing device may also form part of the ventilation mask. Having the gas reservoir and/or the second gas reservoir, and in some cases the gas mixing device, as part of the ventilation mask provides a more compact system which may be advantageous in aircraft where space is limited. Furthermore, providing the individual components of the apparatus as part of a ventilation mask results in a portable ventilation system.

The ventilation gas mixture may comprise at least 15% v/v oxygen, substantially 0%-16% v/v carbon dioxide, and nitrogen.

According to another aspect of the present invention there is provided a ventilation mask configured to supply a ventilation gas mixture to a person, the ventilation mask comprising: a gas mixing device comprising an air outlet; a first gas feed arranged to supply a first gas to the gas mixing device; a gas reservoir comprising an air inlet arranged to receive exhaled air from a person and to store carbon dioxide from the air received via the air inlet, the gas reservoir further arranged to supply the stored carbon dioxide to the gas mixing device via a second gas feed; wherein the gas mixing device is arranged to combine the first gas with the carbon dioxide in order to prepare the ventilation gas mixture, the gas mixing device further arranged to supply the ventilation gas mixture to a person via the air outlet.

The ventilation mask can provide a ventilation gas mixture to a user with relatively small quantities carbon dioxide added to the ventilation gas mixture in order to improve the body's use of the oxygen in the ambient air. By re-using exhaled carbon dioxide from the user's breath and mixing it with ambient air for form the ventilation gas mixture, a lower quantity of emergency oxygen can be kept on board the aircraft, reducing the overall size of the emergency oxygen system. The ventilation mask provides users with a ventilation gas mixture which enables survival at altitude (e.g. between 10,000 ft and 22,000 ft and above), for long periods of time, without adding a significant weight penalty to the aircraft which enables significant fuel and efficiency savings for airlines to be made.

There may also be provided a ventilation mask configured to receive a ventilation gas mixture prepared using an apparatus for preparing a ventilation gas mixture according to any of the above described apparatuses.

According to a third aspect of the present invention there is provided a method of preparing a ventilation gas mixture comprising the steps of: supplying a first gas to a gas mixing device via a first gas feed; receiving exhaled air from a person via an air inlet; supplying the air received from the air inlet to a gas reservoir; storing carbon dioxide from the air exhaled by a person in the gas reservoir; supplying the stored second gas to the gas mixing device via a second gas feed; wherein the gas mixing device combines the first gas with the carbon dioxide in order to prepare the ventilation gas mixture.

The method may further comprise the step of delivering the ventilation gas mixture to a person via a ventilation mask. In some cases, the ventilation mask may be according to any of the above described ventilation masks.

There may also be provided a method of preparing a ventilation gas mixture according to the above described method using an apparatus according to any of the above described apparatuses.

According to a fourth aspect of the present invention there is provided an apparatus for supplying a ventilation gas mixture, comprising: a first gas feed for supplying a first gas; a second gas feed for supplying a second gas; a gas mixing device, via which one of the gases can be added to the other gas to prepare the ventilation gas mixture; wherein the respective gas is deliverable to at least one of the first or second gas feeds from a respective first or second reservoir via a respective first or second pressure regulator; wherein at least one of the reservoirs is embodied as a filter which is configured to store of a gas from air exhaled by a person.

According to a fifth aspect of the present invention there is provided a method for preparing a ventilation gas mixture, comprising the steps of: providing a first gas to a gas mixing device; providing a second gas to a gas mixing device; mixing the first and second gases in the gas mixing device to produce a ventilation gas mixture; wherein the second gas is supplied to the gas mixing device from a filter, the filter comprising a gas from air exhaled by a person.

In other developments there may be provided an apparatus for supplying a ventilation mixture that comprises a first gas feed for supplying a first gas and a second gas feed for supplying a second gas. The apparatus further includes a device, particularly a gas mixer, via which one of the gases may be added to the other gas to prepare the ventilation gas mixture, wherein the proportion of the at least first or second gas in the ventilation mixture can be set variably, wherein the mixing ratio of the first gases and the second gas may preferably be kept constant within prescribed limits for each setting. At the same time, the apparatus is not limited to the use of two gases, but may be supplemented with further gases and/or gas feeds. The respective supplied gas may itself also be a gas mixture and/or the product of a chemical reaction. The gas delivered via a gas feed also does not have to be unchangeable, so that the nature or composition thereof may be variable. For example, it may be possible to deliver oxygen via a gas feed initially, and subsequently to deliver ambient air by the same means. The delivery of at least two gases or gas mixtures for the preparation of a ventilation gas mixture relates primarily to the option of being able to adjust the composition of the ventilation gas mixture variably in this way. However, it is also conceivable to deliver the same gases or gas mixtures to ensure redundancies.

The respective gas may be deliverable to at least one of the first or second gas feeds from a respective first or second reservoir via a respective first or second pressure regulator, particularly controlled by the ambient pressure and/or in time-dependent manner.

The first and/or second pressure regulator may comprise at least one altitude sensor, particularly a pressure sensor, or may receive information on ambient pressure via an external device.

The first and/or second reservoir may have a shut-off valve which may be actuated preferably via the respective pressure regulator, wherein the shut-off valve may preferably comprise an activation unit or may be designed as such, so that a chemical reaction may initiate the preparation of the gas in the reservoir associated with the shut-off valve.

An intermediate reservoir may be arranged downstream of the device via which one of the gases may be added to the other gas to prepare the ventilation gas mixture, which intermediate reservoir may be particularly constructed in such manner that the temporarily stored ventilation gas mixture can be discharged at intervals.

The device, via which one of the gases can be added to the other gas to prepare the ventilation gas mixture, may be arranged downstream of a vacuum valve.

The first reservoir may initially supply oxygen as a first gas or a first gas with an oxygen-content of at least 15% v/v, preferably at least 20% v/v, and/or the second reservoir may supply as a second gas carbon dioxide or a second gas with a carbon dioxide-content of at least 1% v/v, preferably at least 3% v/v.

There may be provided a ventilation mask for ventilation or respiratory support to be used in an apparatus for delivering a ventilation gas mixture, such as the apparatus described above, wherein the ventilation mask comprises the device via which one of the gases may be added to the other gas to prepare the ventilation gas mixture, particularly a gas mixer. The idea of ventilation or respiratory support includes not only providing auxiliary and supervised ventilation, but also influencing the respiratory air for the purpose of obtaining a defined effect.

With regard to ventilation, a fundamental distinction is made between assisted ventilation and supervised (mandatory) ventilation. In this context, a ventilation device used for assisted ventilation serves purely as an auxiliary measure when spontaneous breathing is insufficient. The patient breathes himself and controls the respiratory frequency. On the other hand, in the case of supervised ventilation the ventilation device replaces the body's own respiratory function entirely. However, ventilation masks are used not only in the area of patient ventilation, but also for people in emergency situations, such as loss of pressure in aircraft cabins or who are exposed to other extreme ambient conditions, as is the case for pilots of high-speed aircraft.

The ventilation mask may have one or more connection(s) for feeding the first gas and/or the second gas to the device via which one of the gases may be added to the other gas to prepare the ventilation gas mixture, and/or the first reservoir and/or the second reservoir, wherein preferably at least one of the reservoirs may be embodied as a filter which favours storage of a gas from the exhaled air, particularly of carbon dioxide.

The ventilation mask may comprise the first and/or second pressure regulator. The ventilation mask may have at least one connection for the intermediate reservoir. The ventilation mask may include the vacuum valve.

In another development there may be provided a method for preparing a ventilation gas mixture, comprising the steps of:
providing a first gas;
providing a second gas;
mixing the first and second gases to produce a ventilation gas mixture, wherein the mixing ratio of the first and second gases is controlled, preferably controlled under supervision depending on ambient pressure and/or time, particularly via pressure regulators and/or a gas mixer, wherein the preparation is further preferably initiated depending on ambient pressure. Supervised control proves to be advantageous particularly if for example the change in ambient conditions affects the regulation variable, as in the case of a pressure-dependent mixing ratio, and/or if the controller must modify its control behaviour based on patient data, such as the degree of saturation of a gas component being already reached. A supervised control within the meaning of this disclosure is thus directed to suitability for regulation and corresponding monitoring devices which are part of the control or are directly or indirectly connected thereto for purposes of signal transmission.

The ventilation gas mixture may be stored temporarily and preferably discharged at intervals before it is delivered. A positive negative pressure may be compensated before the ventilation gas mixture is delivered.

The ventilation gas mixture may be delivered via a ventilation mask, particularly a ventilation mask as described above.

In a further development there may be provided the use of the apparatus as described above, a ventilation mask as described above and/or a method as described above for ventilating persons with limited freedom of movement as needed and/or generally in the case of hyperventilation and/or for ventilating persons in aircraft, particularly in cases of loss of pressure.

In a further development there may be provided the use of the apparatus, the ventilation mask and/or the method for ventilating persons in aircraft, particularly in the event of loss of pressure. This relates both to use for the pilots, the cabin crew and for the aircraft passengers. The variant in each case is preferably adapted to the respective requirements profiles of the specific groups. Thus for example for the cabin crew a variant is advantageous that to the extent possible does not limit freedom of movement, and in particular may be used while moving around. This also relates to groups of individuals for whom wearing a ventilation mask may be intended for prolonged periods.

In a further development there may be provided the use of the apparatus, the ventilation mask and/or the method for delaying a critical oxygen saturation during ventilation of persons, particularly in hypoxia applications and/or as countermeasure for hypocapnia risks. In this context, applications are conceivable in high elevation sports, particularly in mountainous regions with correspondingly lower oxygen contents in the air.

In a further development there may be provided the use of the apparatus, the ventilation mask and/or the method as a countermeasure in cases of risk of hypocapnia.

In a further development there may be provided the use of the apparatus, the ventilation mask and/or the method for stabilizing the blood pH value in individuals for purposes of administering oxygen.

In a further development there may be provided the use of the apparatus, the ventilation mask and/or the method for pre-oxygenation prior to intubation.

As will be appreciated any numerical values specified throughout are not exact and can include small variations (such as but not limited to standard mathematical rounding conventions) either side of the numerical value which bring about the same technical effect as the specified value.

As will be appreciated all of the above aspects and developments may be combined together in any combination and they may be used together in combination with each other.

BRIEF DESCRIPTION OF DRAWINGS

Features and practical uses of the invention will be described in the following text also on the basis of exemplary embodiments with reference to the drawing.

In the drawings, the figures show.

SPECIFIC DESCRIPTION

Figure 1:
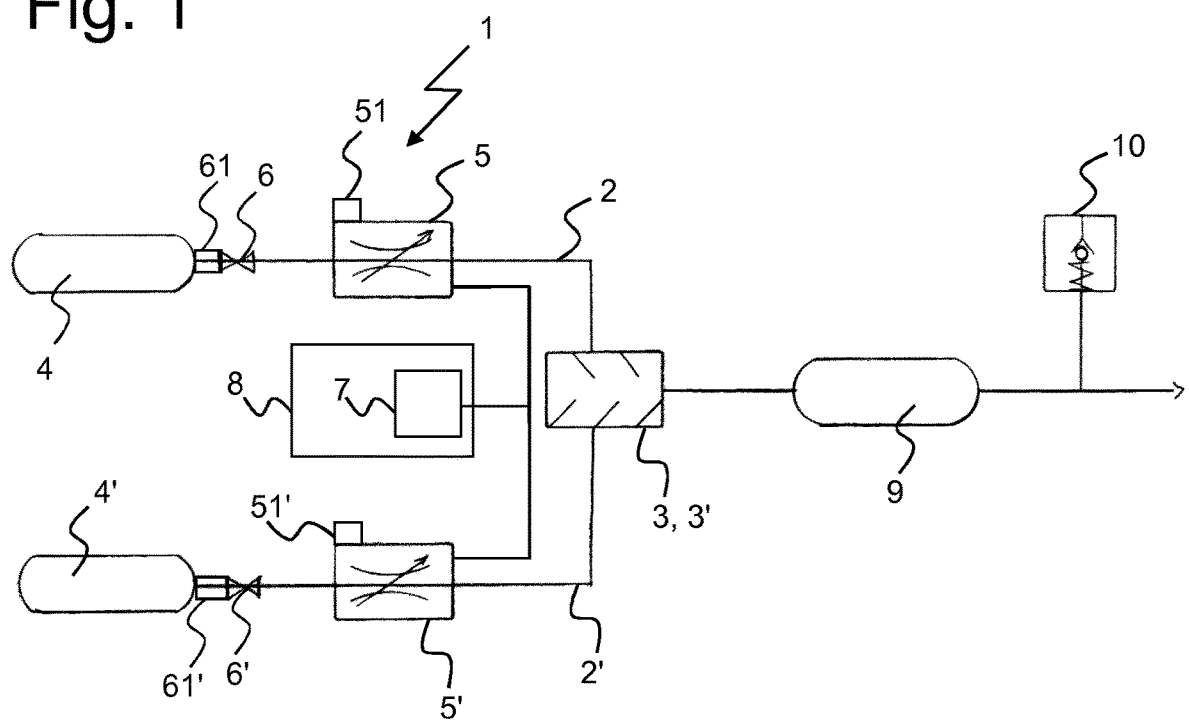
FIG. 1: a schematic representation of an apparatus as an example of an apparatus for preparing a ventilation mixture.

FIG. 1 shows an apparatus 1 for preparing a ventilation mixture with a first gas feed 2 for delivering a first gas and a second gas feed 2' for delivering a second gas. In this context, the term gas also refers to gas mixtures or also gases or gas mixtures as a product of chemical reaction. The terms gas and gas mixture may be used synonymously and in the following text will be used in both forms solely for illustrative purposes in examples. Regarding the production of a gas or gas mixture from a chemical reaction, this will no longer be stated explicitly as a further option for producing gas continuously throughout the text. Instead it is considered to be implied as an option when gases and gas mixtures are mentioned. For the purposes of the usage options, the first gas is preferably oxygen or a gas mixture with an oxygen content of at least 15% v/v, particularly at least 20% v/v. The second gas is preferably carbon dioxide or a gas mixture with a carbon dioxide content of at least 1% v/v, particularly at least 3% v/v. If the preparation of further gases or gas mixtures is intended, the variants described in the embodiments may be adapted therefor, for example a third gas feed. The preparation of the ventilation gas mixture via a corresponding device may then also deliver this additional gas. As an example, the use of a third gas feed to deliver ambient air is cited, by which a ventilation gas mixture consisting of all three gas feeds or only a predefined selection of the three gas feeds may be prepared variably. At higher altitudes, a ventilation gas mixture might be prepared from oxygen via the first gas feed and carbon dioxide via the second gas feed or a ventilation gas mixture of oxygen via the first gas feed, carbon dioxide via the second gas feed and ambient air via the third gas feed, while at lower altitudes only a ventilation gas mixture consisting of carbon dioxide and ambient air is prepared. The compositions of the respective ventilation gas mixtures in such context are preferably prescribed according to altitude and/or pressure.

The apparatus 1 in FIG. 1 further includes a device 3 via which one of the gases may be added to the other gas to prepare a ventilation mixture. The term "addition" may also be understood to be a merging of the gases and in this context it is not imperative to define whether one gas if fed into the second or vice versa. It is also not precluded that further gases may be fed into the ventilation gas mixture or further products may be added to the mixture subsequently. Accordingly, a ventilation gas mixture is understood to be a gaseous product which is used for ventilation or for respiratory support either alone or as a component of a subsequent combined ventilation gas mixture. The device 3 for feeding the one gas to the other gas may preferably be embodied as a gas mixer 3'.

The percentage of the at least first or second gas in the ventilation gas mixture is variably adjustable. For this purpose, as one option the apparatus 1 includes a reservoir 4, 4, for at least one of the gases, from which the respective gas may be delivered to the associated gas feed via a pressure regulator 5, 5'. The apparatus 1 shown in FIG. 1 has such a first reservoir 4 and a second reservoir 4' for both the first and the second gas, each with a first pressure regulator 5 and a second pressure regulator 5' respectively. The use of pressure regulators 5, 5' enables the required pressure and/or the required quantity of the respective gas(es) to be adjusted. The pressure regulators 5, 5' also quantity regulators thus also serve to set a constant mixing ratio of the gases, which may also be varied according to specification. Alternatively or additionally thereto, the gas mixer 3, and/or the device 3 may also be designed so as to keep the required mixing ratio of the gases constant in each case. In this case, the gas mixer is preferably also equipped with an altitude sensor or the capability to receive signals via an external device 7 for actuation depending on ambient pressure, as will be described in detail later with reference to the pressure regulators.

In general, it should be noted that the constant mixing ratio of the first and second gases may be established with reference to both absolute values and relative values. Depending on tolerability for deviations from a prescribed value or ratio, it is understandable that the constancy refers to values within prescribed limits.

Unlike the use of a first pressure regulator 5 and a second pressure regulator 5' as shown in FIG. 1, it is also possible that only a first pressure regulator 5 or a second pressure regulator 5' may be present. In this case, a second gas which may delivered at a variable feed rate via a second pressure regulator 5' is fed into a gas flow of a first gas which is under constant pressure to produce a required mixing ratio. In this way it is easily possible to retrofit apparatuses that are already installed and are only equipped with a constant ventilation gas preparation system.

Although the pressure regulators 5, 5' are shown schematically in the area of the respective gas feeds 2, 2' in FIG. 1, they may alternatively be attached to the respective reservoirs 4, 4, as well. In some cases the pressure regulators 5, 5' may be attached to a ventilation mask.

In a further development, the first pressure regulator 5 and/or the second pressure regulator 5' is/are controlled by the ambient pressure. In this way, the proportional gas feed quantity of the first and/or second gas may be altered in a desired composition of the ventilation gas mixture dependent on an ambient pressure. For this purpose, the first pressure regulator 5 and/or the second pressure regulator 5' may be equipped with an altitude sensor 51, 51' or it/they may receive the information regarding ambient pressure via an external device 7. In turn, the external device 7 may itself comprise an altitude sensor, or this may be separate and forward its signal to the external device 7. An external device 7 may also be the controller, for example. The altitude sensor 51, 51' may be embodied as a pressure sensor. In some developments, individual sensors which measure the partial pressure of oxygen and/or carbon dioxide may be employed in isolation or combination with a height or pressure sensor. Alternatively, an evaluation of GPS data may serve to determine an ambient pressure or a value that is usable as equivalent therefor. The possibility also exists to use both the information from an altitude sensor 51, 51' included as part of a pressure regulator and the signal from an external device 7 to actuate the first and/or second pressure regulators 5, 5'. This may serve as a redundant design of the ambient pressure determination or it may also be used for monitoring purposes. If ambient pressure signals differ from each other within prescribed limits, control of the first and/or second pressure regulator 5, 5' may by assumed via the altitude sensor 51, 51' built into the pressure regulator or the external device 7 depending on prioritisation or if a failure is detected.

Alternatively or in addition to ambient pressure-dependent actuation of the pressure regulator, however, a time-dependent variable setting of the mixing ratio of the first and second gases may also be provided. For certain ventilation or respiratory support scenarios, it may be advantageous to increase or reduce a mixing ratio only slowly or from an initiation point in time to a time delay. Scenarios are also conceivable in which a certain mixing ratio is only to be delivered for a defined period. Like the ambient pressure-dependent actuation, the time-dependent actuation of the mixing ratio is also applicable similarly in all components of the apparatus that contribute to controlling the mixing ratio and/or fulfil the function instead of the pressure regulators, such as the gas mixer 3' for example. Regulations or default settings dependent on consumption values or condition-dependent combinations of control instructions are also possible alternatively or additionally.

For the purposes of the described performance capabilities, the apparatus 1 according to FIG. 1 has a first pressure regulator 5 located downstream of the first reservoir 4 and a pressure regulator 5' located downstream of the second reservoir 4'. The two pressure regulators 5, 5' each comprise an altitude sensor 51, 51'. This is embodied here as a pressure sensor. It should be noted that "sensor" is intended to cover both an electrical device as well as a barometric capsule having a mechanical connection to a valve. In the latter example, changes in altitude would change the capsule shape, exerting a mechanical force on the valve to adjust the gas flow settings.

In one variant, the signal from the altitude sensor 51, 51' of the first or second pressure regulator 5, 5' may also be used as the signal for the respective other pressure regulator. For example, it is possible for only the first pressure regulator 5 to include an altitude sensor 51 and to forward the signal to the second pressure regulator 5' as well, so that the first pressure regulator 5 may be considered an external device. However, with a view to redundancy and/or expected different ambient pressure conditions, it may also be advantageous to assign a dedicated altitude sensor 51, 51' to each pressure regulator 5, 5'. For the purpose of preparing a ventilation gas mixture, the signal that substantially corresponds to the ambient pressure upon feeding for ventilation or respiratory support or which is in a known or ascertainable proportion to the local ambient pressure at the application site is to be preferred. For this purpose, FIG. 1 shows the external device 7, which in this case is a part of the controller 8 and transmits a signal of the ambient pressure at the application site, which can be compared with the signals from the altitude sensors 51, 51' of the pressure regulators 5, 5.

The first and second reservoirs 4, 4, of the apparatus 1 shown in FIG. 1 each have a shut-off valve 6, 6' which is actuated via the respective pressure regulator 51, 51'. This optional shut-off valve 6, 6' comprises an activation unit 61, 61' or is designed as such, so that a chemical reaction initiates the preparation of the gas in the reservoir associated with the shut-off valve. Alternatively or in addition thereto, the shut-off valve 6, 6' and/or the activation unit 61, 61' may be actuated manually, particularly mechanically, and/or by an electronic signal, for example an opening signal from the controller or an external signal. Alternatively, the activation unit 61, 61' may also be included in the respective reservoir 4, 4'.

The apparatus 1 according to FIG. 1 also has an intermediate reservoir 9. This optional intermediate reservoir 9 is arranged downstream of the device 3 through which one of the gases is added to the other gas. The optional intermediate reservoir 9 enables at least partial intermediate storage so that a larger quantity of the ventilation gas mixture can be made available to the consumer. This can then take place at intervals that are periodic, for example according to the individual's own or a predetermined breathing rate, or according to needs. In this context, such an intermediate reservoir 9 does not necessarily have to be located downstream of the device 3 and thus assigned to the ventilation gas mixture; it may also be used alternatively or additionally in the same way for the intermediate storage and/or intermittent discharge of the first and/or second gas.

The apparatus 1 according to FIG. 1 is also equipped with a vacuum valve 10 located downstream of the intermediate reservoir 9. This optional vacuum valve 10 has no effect on the operating principle by which the ventilation gas mixture is prepared as such, but it is able to prevent or at least reduce a negative pressure that is perceptible by the consumer. Such a perceptible negative pressure may be the result of excessive inhalation, as occurs for example during fear-induced hyperventilation. The perceptible negative pressure may evoke unpleasant, alarming feelings which tend to aggravate the excessive inhalation further. This may be counteracted with the vacuum valve 10. The vacuum valve may also be located downstream of the device by which one of the gases is added to the other to prepare the ventilation mixture, which happens if the intermediate reservoir 9 is omitted.

Figure 2:
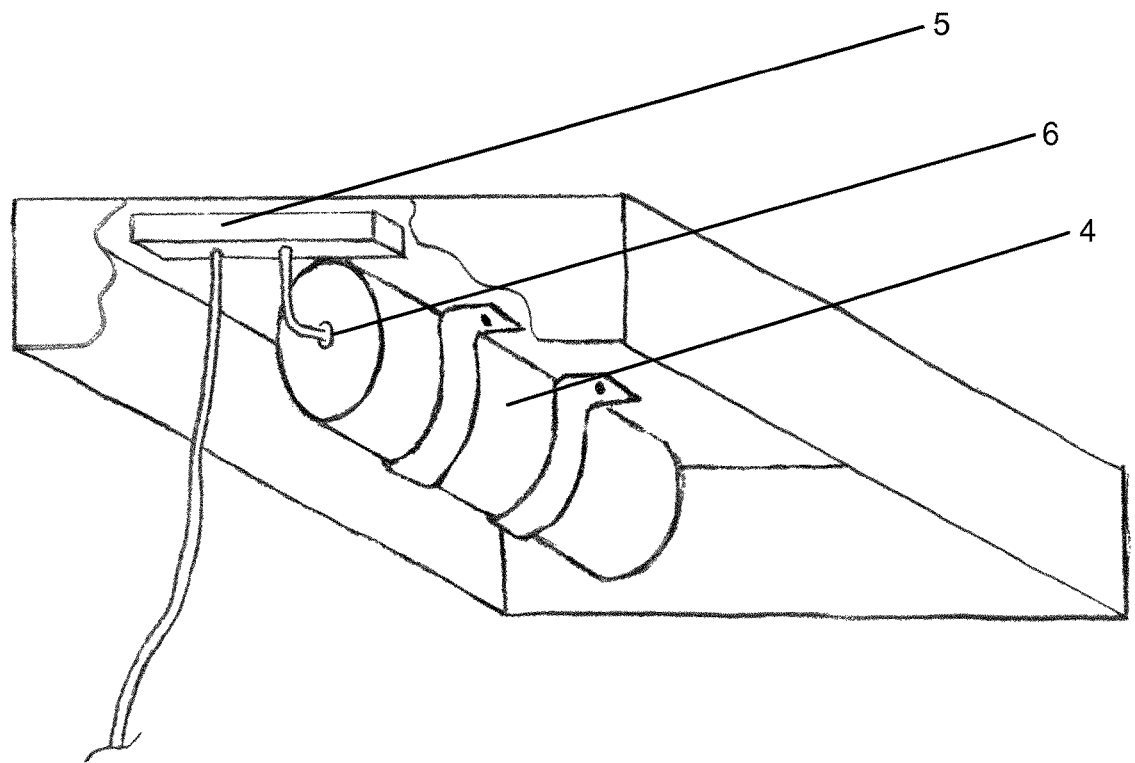
FIG. 2: a possible arrangement for a first reservoir.

FIG. 2 represents a possible arrangement of a first reservoir 4, in this case for storing and discharging oxygen, a first shut-off valve 6 and a first pressure regulator 5. The compact arrangement is particularly suitable for installation in the cabin or cockpit of an aircraft. Given the use that would be typical in an aircraft setting, such as ventilation or respiratory support in the event of loss of pressure in the aircraft cabin, the ambient pressure-dependent control of the first pressure regulator 5 would seem to lend itself particularly advantageously to this situation.

Figure 3:
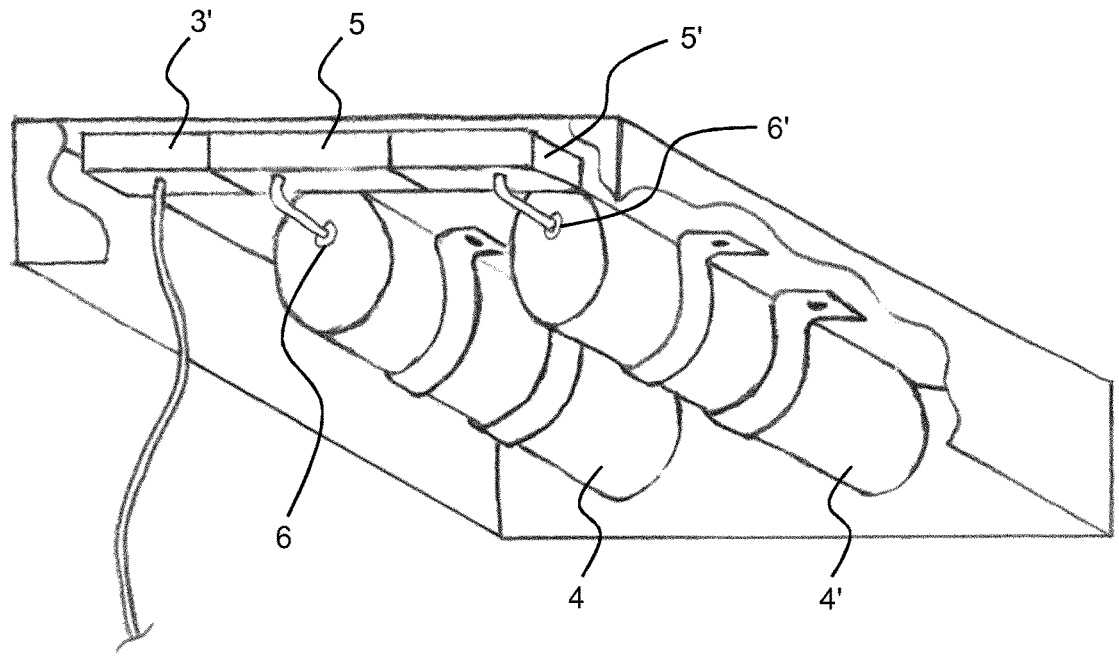
FIG. 3: a possible arrangement for a first and second reservoir.

In a further development according to FIG. 3, the arrangement shown in FIG. 2 additionally shows a second reservoir 4', in this case for discharging and storing carbon dioxide, a second shut-off valve 6' and a second pressure regulator 5'. In order to deliver the ventilation gas mixture via the arrangement, said arrangement also has a gas mixer 3' as a corresponding device 3. The arrangement according to FIG. 3 may thus deliver the ventilation gas mixture directly, whereas the second gas is fed to the arrangement according to FIG. 2 by some other means centrally or decentrally. Despite the expansion to the arrangement in FIG. 3, it is still compact enough to lend itself to installation in the cabin or cockpit of an aircraft. In the same as was explained with reference to FIG. 2, an ambient pressure-dependent control of the pressure regulator 5, 5' is particularly advantageous for a typical use in aircraft.

Figure 4:
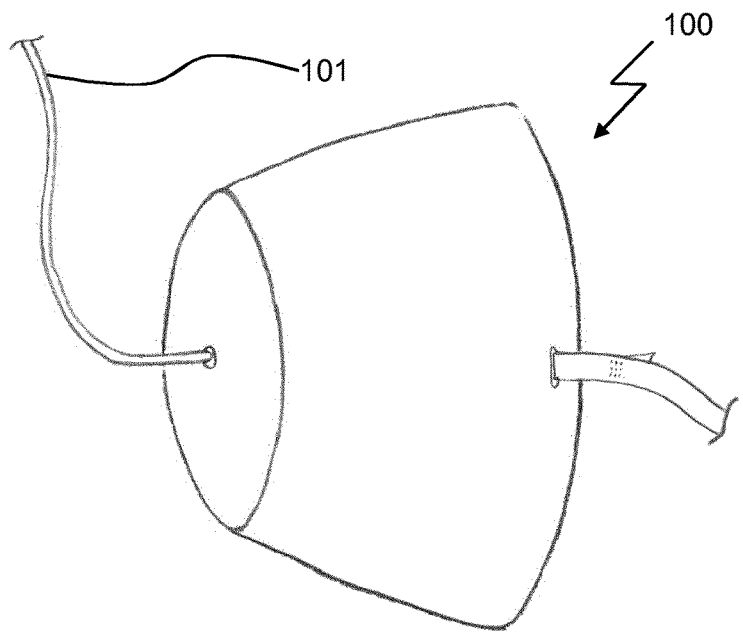
FIG. 4: an example of a ventilation mask for connection to an apparatus for preparing a ventilation gas mixture.

The apparatus 1 in the various forms thereof is suitable for connection to a ventilation mask 100 for ventilation or respiratory support, as is shown in FIG. 4. The ventilation mask 100 has at least one connection 101 for feeding the ventilation gas mixture.

Figure 5:
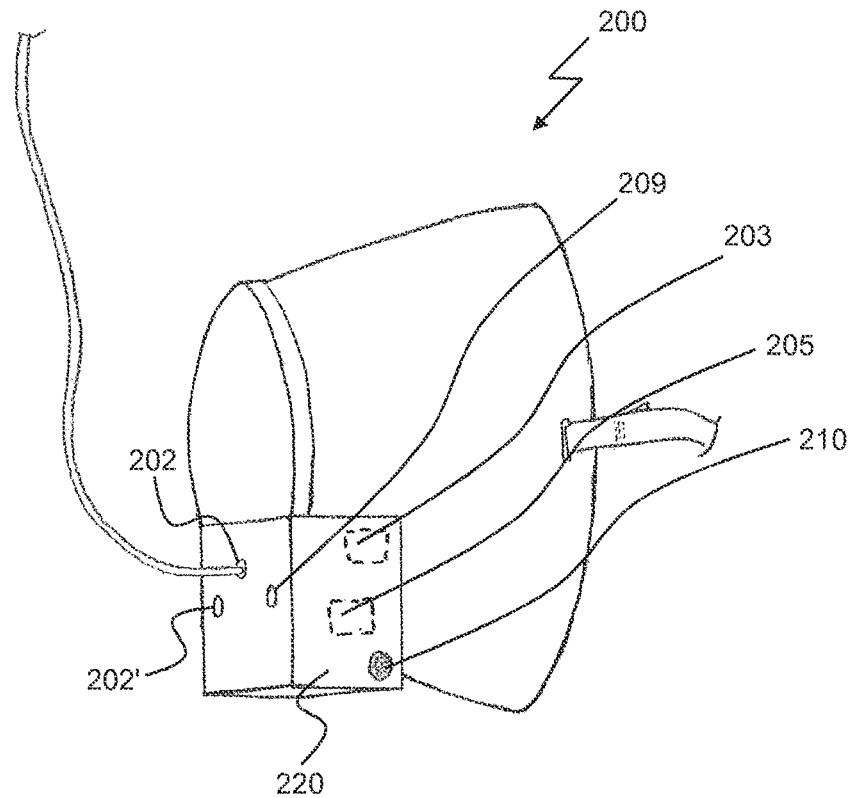
FIG. 5: an example of a ventilation mask for ventilation or respiratory support in an apparatus for preparing a ventilation gas mixture.

But the apparatus 1 does not necessarily have to be understood as a system to be considered separately from a ventilation mask. A ventilation mask may assume functionalities and corresponding physical elements of the apparatus 1, so that it is intended for use in the apparatus 1. Such a ventilation mask for ventilation or respiratory support in the apparatus 1 is represented in FIG. 5 as ventilation mask 200. The ventilation mask 200 has a gas mixer 203 as a device via which one of the gases is added to other gas to prepare the working gas mixture. The gas mixer 203 may be replaced by other devices which fulfil the function of a corresponding device. A first gas, in this case oxygen, is fed to the gas mixer 203 via the connection 202. A second gas may be introduced into the gas mixer 203 in a similar way via a connection 202'. But alternatively or additionally thereto, the second gas may also be fed to the gas mixer 203 via the ambient air. Such a feed (not shown) enables the supply of ambient air itself or also of certain components of the ambient air, particularly carbon dioxide, by the provision of corresponding filters. The ventilation mask 200' also has a first pressure regulator 205, which is located upstream of the gas mixer 203. The first pressure regulator 205 is preferably controlled by the ambient pressure. The gas mixer 203 and the first pressure regulator 205 are represented in FIG. 5 not as a separate component but enclosed by a housing 220. Even though the connection 202 for the first gas and the connection 202' for the second gas are routed into the housing 220, it is evident that the first and second gases are fed into the gas mixer 203 directly or indirectly by the connections 202, 202'. The housing 220 is also equipped with a connection 209 for an optional intermediate reservoir 9, wherein such a connection 209 is not essential since the intermediate reservoir 9 itself is also optional. The connection 209 does not necessarily serve to feed a stored gas into the gas mixer; it may also be provided that the ventilation gas mixture prepared by the gas mixer 203 is stored temporarily in the intermediate reservoir 9. Although only one connection 209 is shown, it is clear that provision must be made to return the temporarily stored ventilation gas mixture or other gas via the connection 203 or another feed so that it reaches the gas mixer 203 in the case that the gas is stored temporarily or it reaches the consumer in the case that the ventilation gas mixture is stored temporarily. Finally, FIG. 5 also shows a pressure relief valve 210 which is arranged in such manner that the ventilation gas mixture is fed to the consumer without perceptible negative pressure.

Figure 6:
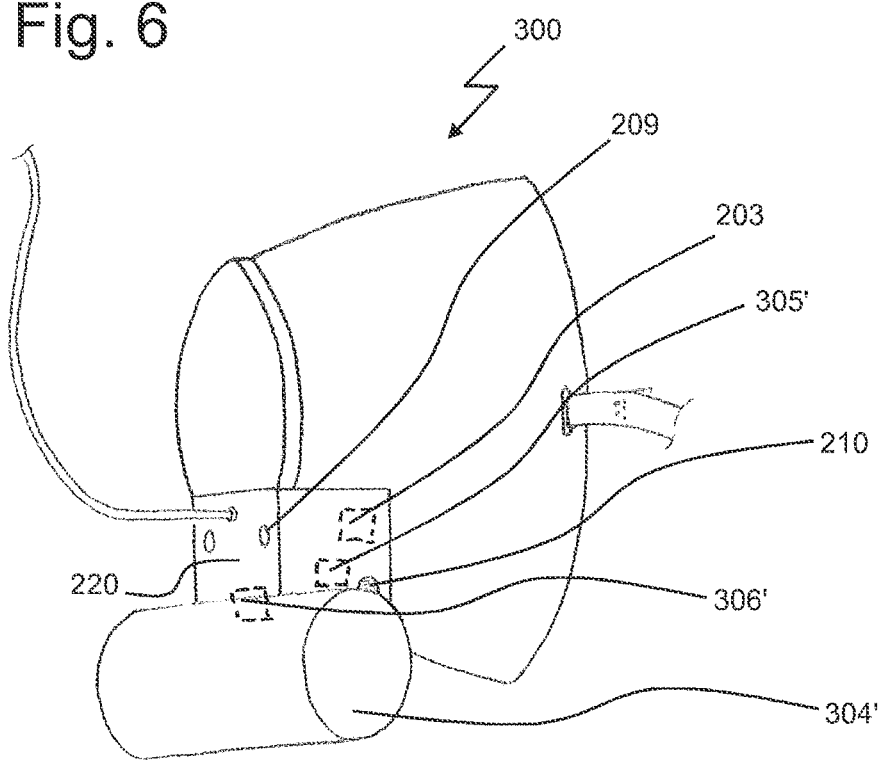
FIG. 6: a further example of a ventilation mask with a reservoir for ventilation or respiratory support in an apparatus for preparing a ventilation gas mixture.

In a further development, as represented in FIG. 6, besides the components described earlier with reference to FIG. 5, denoted here with the same reference numbers, the ventilation mask 300 also has a reservoir 304', for the second gas, in this case carbon dioxide, which is understood to be the second reservoir 304', because of its assignment to the second gas. The second reservoir 304', or its feed to the gas mixer 203 comprises a second shut-off valve 306' which belongs to the second gas. The second gas is fed to the gas mixer via a second pressure regulator 305', which is controllable by the ambient pressure. If a ventilation gas mixture is to be produced using air enriched with carbon dioxide, the connection 202 may be replaced or provided additionally by a feed for ambient air.

Figure 7:
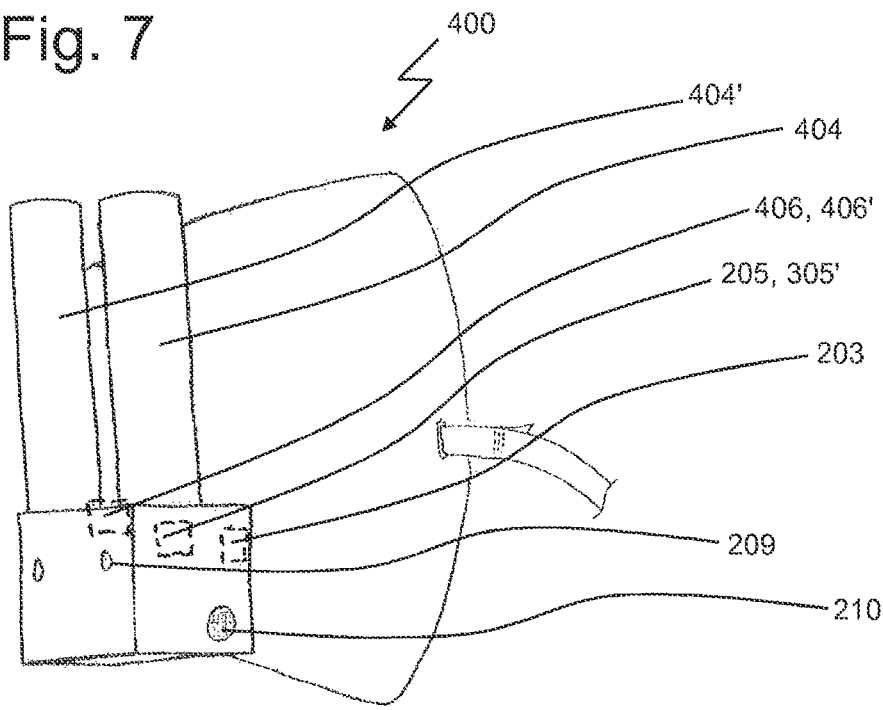
FIG. 7: a further example of a ventilation mask with two reservoirs for ventilation or respiratory support in an apparatus for preparing a ventilation gas mixture.

With reference to FIG. 7, a further development is described in which the ventilation mask 400 is able to deliver the ventilation gas mixture without an external gas feed as an additional device. For this, the ventilation mask 400 itself is equipped with a first reservoir 404 and second reservoir 404', each having shut-off valves 406, 406' or a common shut-off valve. And additional connections are also conceivable for the first and/or second gas as supplementary measures, in order to be able to continue ensuring an emergency supply in the event of a malfunction and consumption of the gas in one of the reservoirs.

Figure 8:
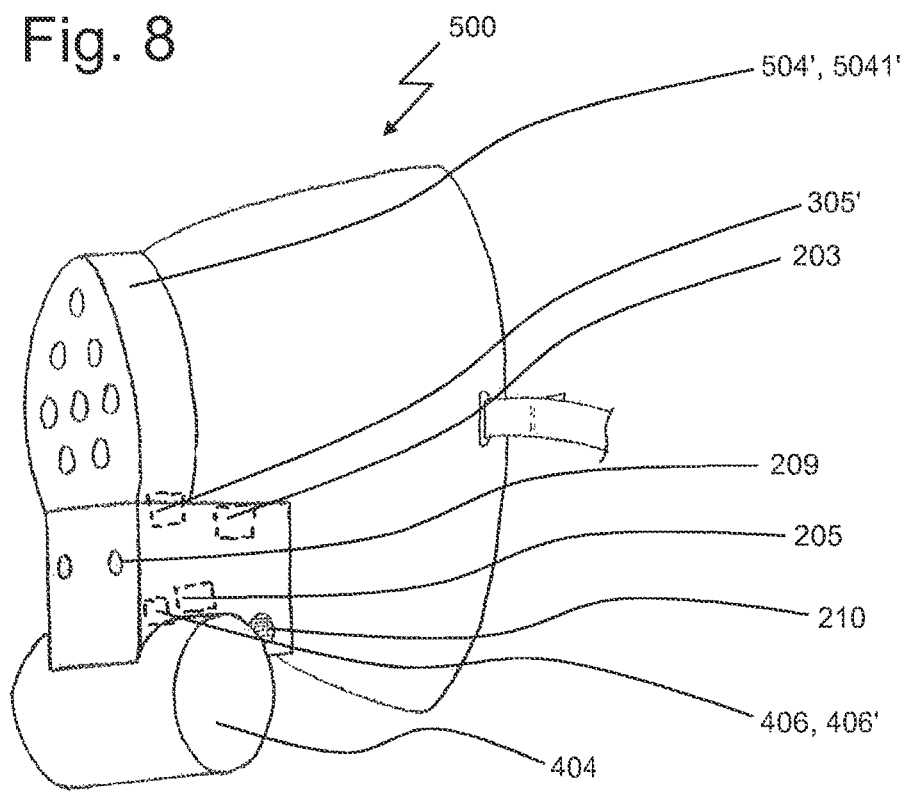
FIG. 8: a further example of a ventilation mask with two reservoirs and a filter attached to a reservoir for ventilation or respiratory support in an apparatus for preparing a ventilation gas mixture.

According to FIG. 8, a variant includes a ventilation mask 500 with a second reservoir 504, that comprises a filter 5041', so that components from the exhaled air are made available to the second reservoir 504' in targeted manner for storage and discharge of a second gas. In a usage variant, the second reservoir 504, is a carbon dioxide reservoir, to which carbon dioxide from the exhaled air is fed via the filter 5041'. As was described earlier with reference to FIG. 6, a feed for ambient air may be provided instead of or additionally to the first reservoir 404.

Figure 9:
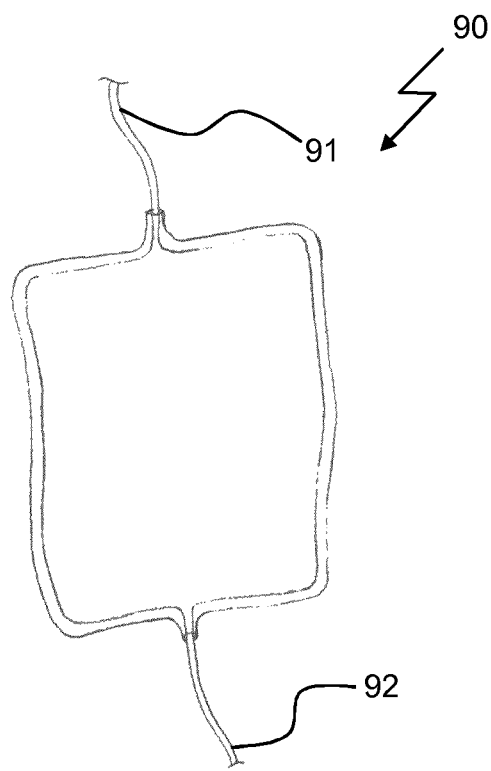
FIG. 9: an example of an intermediate reservoir for an apparatus or ventilation mask.
Figure 10:
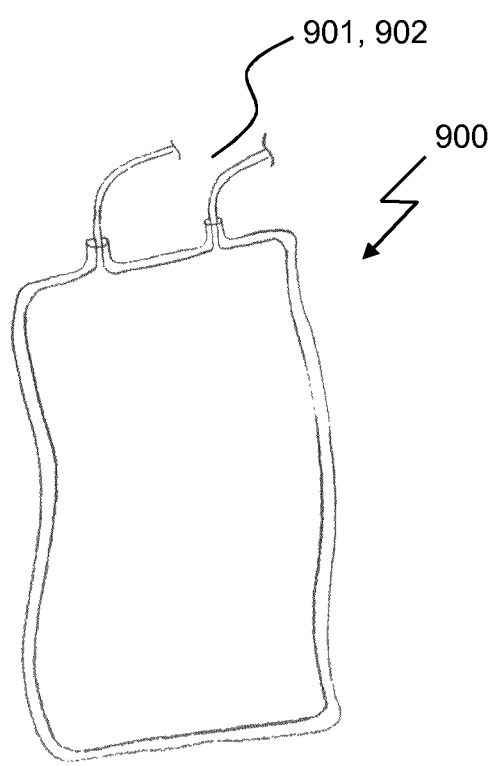
FIG. 10: a further example of an intermediate reservoir for an apparatus or ventilation mask.

FIGS. 9 and 10 show different variants of an intermediate reservoir 90, 900. The intermediate reservoir 90 in FIG. 9 has an inlet connection 91 at one end thereof, which serves to feed gas into the intermediate reservoir 90. The introduced gas may be a ventilation gas mixture from a corresponding device 3, a gas mixer 3' for example, or also a first or second gas which is to be stored temporarily before being forwarded into device 3, via which one gas is to be added to the other gas. An outlet connection 92 at the end of the intermediate reservoir 90 opposite the inlet connection 91 serves to forward the gas that is to be discharged from the intermediate reservoir 90. In the case of a first or second gas, this is then fed to the device 3 for mixing the gases to produce a ventilation gas mixture or, if it is already the ventilation gas mixture itself which is stored temporarily here, it is delivered to the consumer. For the purpose of the operating method of the intermediate reservoir 90, it is not critically important where the inlet connection 91 and the outlet connection 92 are located, particularly whether they are opposite one another. Depending on where they are used, for example in an apparatus in which the gas flows through the intermediate reservoir in one direction, the arrangement in which the connections are opposite one another in the direction of gas flow is advantageous.

The intermediate reservoir 900 according to FIG. 10 shows a variant in which the inlet connection 901 is arranged beside the outlet connection 902. The side-by-side arrangement lends itself advantageously to use with a ventilation mask, because long connection lines are avoided.

Figure 11:
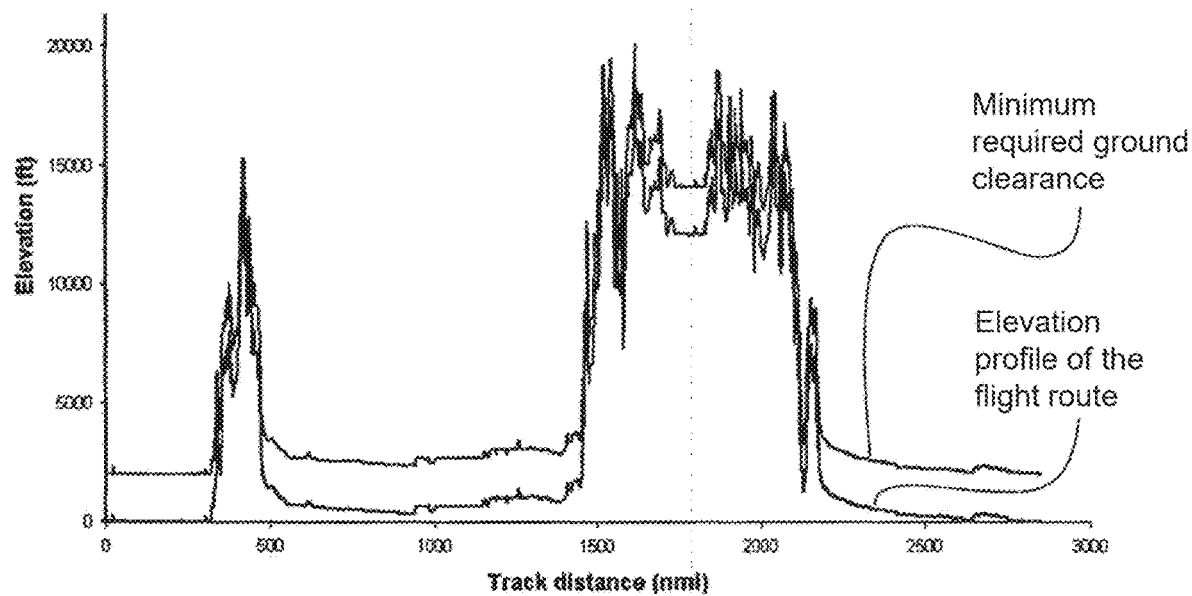
FIG. 11: an altitude profile of a flying route with necessary minimum distance from the ground, which is superimposed over the altitude profile.

Regarding the use and for the purpose of explaining the context thereof, reference is made to FIGS. 11 to 14. The altitude profile associated with a direct route between two airports is represented in FIG. 11. The diagram shows two curves, wherein the lower curve indicates the geographical altitude profile. Superimposed on this is the minimum required distance above the ground which an aircraft must be able to maintain at every point of the flight route. It is therefore imperative that each of the prescribed descent profiles is above the mandatory ground clearance line.

Figure 12:
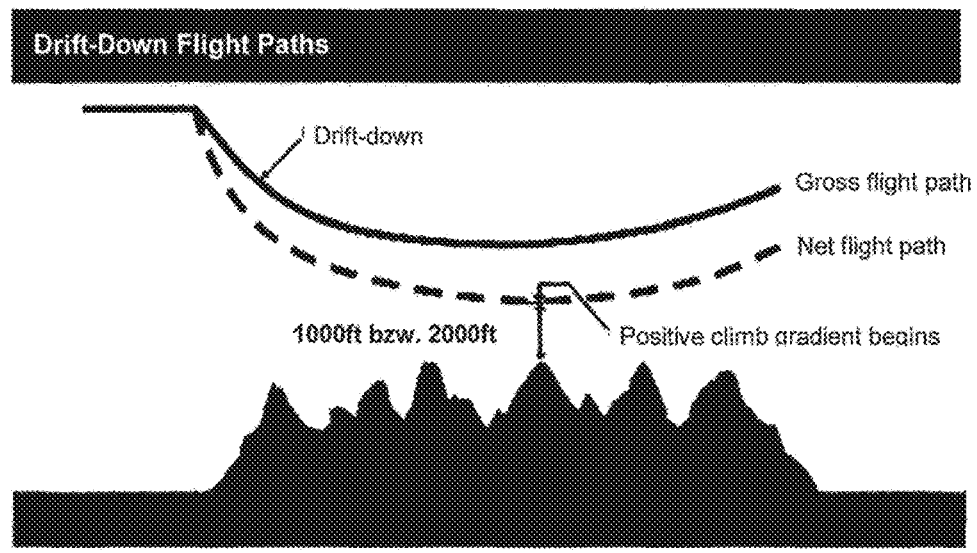
FIG. 12: a typical emergency descent profile of an aircraft towards a lower flight altitude.
Figure 13:
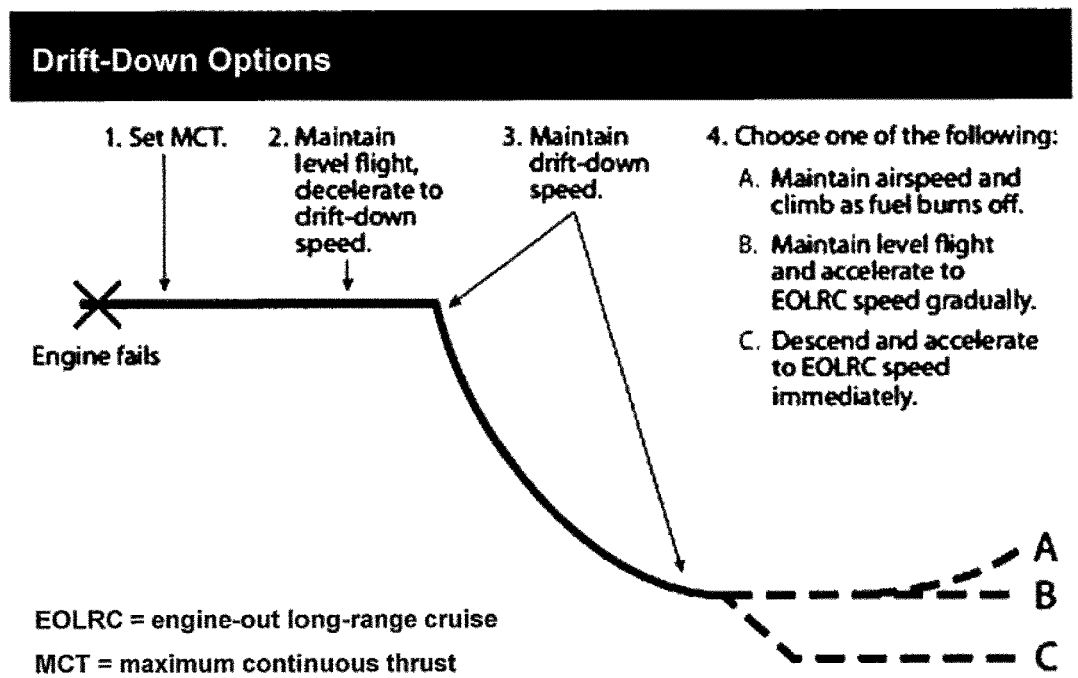
FIG. 13: procedure with options A, B, C in a descent during an engine failure scenario.

FIG. 12 illustrates a typical emergency descent profile of an aircraft following an engine failure. Both the actual trajectory (net flight path) and the idealized trajectory (gross flight path) as developed in flight route planning are indicated. In the event of engine failure during flight, a positive climb gradient must be attained after drift-down, when the aircraft is at least 1,500 ft above the (emergency) landing site. The positive climb gradient is indicated in FIG. 13 at the lowest point of the flight path (at least 1000 ft of vertical clearance above the ground or 2000 ft above elevated terrain). If a fully loaded commercial aircraft cannot fulfil the standards shown at every stage of its flight route, it is not permitted to fly that route.

An emergency escape route system complying with the safety regulations has been developed for all flight routes over high altitude territories. One such system is shown using the example of a mountain range for the flight route of FIG. 12. Route planning is determined primarily by the limited amount of oxygen in the cabin for supply to crew and passengers mentioned in the introduction. A route along this massif, which would thus constantly pass over the high altitude terrain, would therefore not be permitted. In practice, local and aviation-related factors such as wind, temperature, local pressure, weight etc. can also lead to minor deviations from a potential route and therefore need to be determined specifically. It should be noted here that aircraft which fly such a specific route are equipped with corresponding high-capacity emergency oxygen systems, as will be explained in the following section.

Some passenger aircraft and business jets are equipped with high-capacity emergency oxygen systems, also known as burning systems (due to the heat generation resulting from the chemical reaction, by means of which oxygen can be produced aboard). Accordingly, a small number of airliners that cover long distances over high mountain regions are equipped with such high-capacity oxygen devices. However, the oxygen tanks involved and the essential equipment involved result in additional weight, which is detrimental to flight performance—especially in the event of an engine failure, when only a reduced number of engines are still providing thrust. In such a scenario, the effective resulting OEI (one-engine inoperable) service ceiling depends on a number of factors, including the number of engines that still remain operative, and also particularly on the weight of the aircraft. The flight team needs to adapt the procedure of an emergency drift-down to these conditions with the greatest precision. FIG. 13 shows the possible options. In each case, as soon as an engine fails, the maximum continuous thrust is set as the first measure and then an emergency descent is initiated at a defined drift-down speed. Depending on the situation, a decision is then made regarding whether to maintain airspeed after the drift-down and to climb constantly to a higher flight altitude with continued fuel consumption (A). In another situation, the flight altitude is maintained for the remainder of the flight (B) or altitude is reduced further (C) and airspeed is finally accelerated to engine-out long-range cruise speed. If the required height of the flight path, i.e. at least the altitude required by option C, cannot be attained further along the airway after a drift-down due to high-altitude terrain, the aircraft's payload must be reduced, for example, by partially emptying or burn off of fuel, which allows a higher flight altitude (A) to be reached. However, this is contingent on an emergency landing site being available within a foreseeable distance. The weight of the aircraft is always a negative factor in an engine failure scenario. There is a conflict of objectives between solving artificial respiration problems in the event of cabin depressurization and the required descent scenarios in case of engine failure. If the need to supply oxygen to the aircraft occupants takes precedence due to the given flight route, the weight disadvantage of a more efficient oxygen supply system is accepted. The additional time per meter of altitude gained thereby in a cabin pressure loss scenario allows longer escape routes, by which multiple off-track escape areas may be accessed. On the other hand, if the weight disadvantage cannot be compensated any longer, the route cannot be flown, and this is most often the case with routes over extended high mountain areas.

Figure 14:
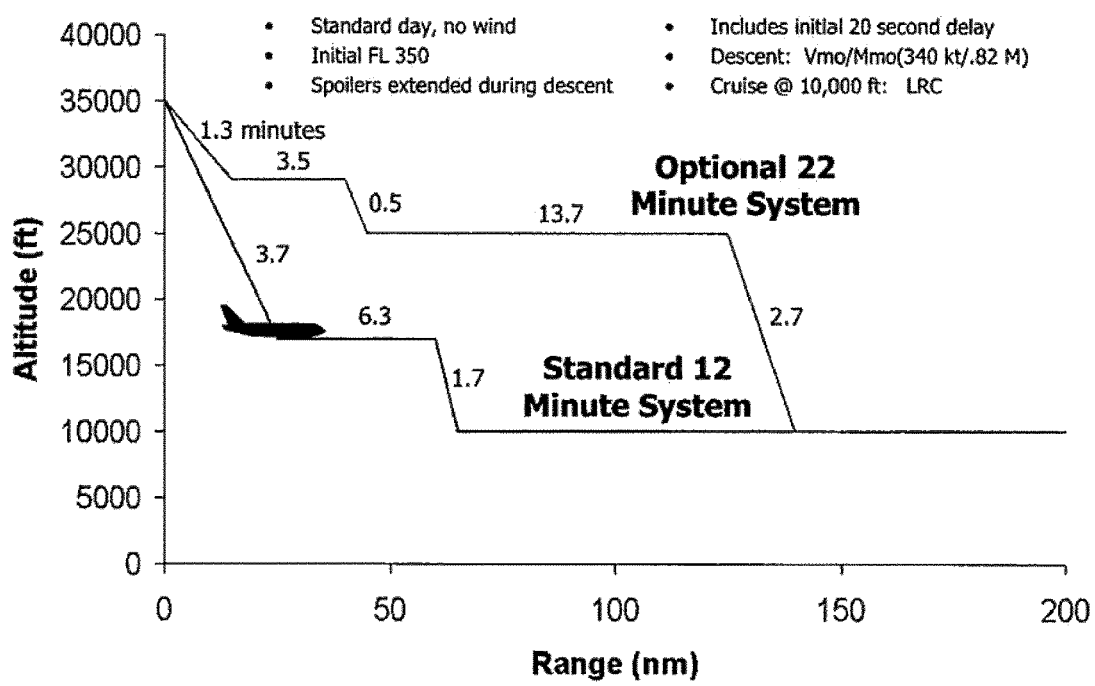
FIG. 14: an emergency descent profile for a 737-700 CFM56-7 in the event of pressure loss in the cabin according to Boeing for a standard descent in 15 minutes and optional descent in 22 minutes, in compliance with ICAO regulations.

In the event of loss of pressure in an aircraft cabin, the specific provisions of ICAO apply. The specific descent profiles prescribed by different aircraft manufacturers or airlines respectively are derived therefrom. For example, two different drift-down profiles may be provided, a standard descent profile and an optional descent profile for exceptional routes. Two such profiles with specific values determined by Boeing are shown in FIG. 14, namely a 15-minute standard profile and an optional 22-minute profile. The magnitudes of these values are the same for all aircraft manufacturers and airlines. Following a cabin depressurization incident, an aircraft of the manufacturer Boeing (The Boeing Company) must have descended to 14,000 ft within 15 minutes or 22 minutes respectively depending on its certification. At the same time, the intermediate altitudes and intermediate times specified in the respective profiles must also be observed. A flight route must be selected such that an aircraft can adhere to these altitudes and times at all times. Thus, when flying over extensive high mountain ranges, detours must be considered so that if a loss of cabin pressure occurs the aircraft can adopt the prescribed descent profile and so descend to a lower altitude quickly enough at all times. More direct flight routes over extensive high mountain areas can almost only be flown by cargo aircraft nowadays, because these carry a greater oxygen supply for the crew than is possible for commercial aircraft. As described previously, the flight path must also be planned taking into account the possibility of an engine failure, in which case the descent profile in FIG. 12 is decisive. Modern airliners are able to fly at considerably higher altitudes after an engine failure than those specified by the profiles in case of cabin depressurization. As a consequence, the limitations imposed on potential flight routes are primarily determined by a potential cabin pressure loss, specified by the emergency descent profiles according to FIG. 14. In general, all escape routes possible in case of cabin pressure loss are equally suitable in the event of an engine failure, but conversely a flight route that is suitable for an engine failure scenario must meet the required time conditions determined by the emergency oxygen system aboard in order to qualify. This reduces the number of potential escape routes considerably. As a consequence, high-altitude areas like the Central Asian mountain regions or the Andes are only open to limited passenger air traffic.

In a conventional cabin pressure loss scenario it is assumed that the engines are fully functioning, which in principle allows airspeeds higher than in the event of engine failure. One might therefore expect that obstacles such as high-altitude terrain could more likely be overflown within the prescribed time interval, and consequently the requirements imposed on route planning would be less stringent. In reality, however, it must be assumed that cabin depressurization is caused initially by a structural failure, so that the airspeed must be adjusted immediately, that is to say reduced. Therefore, it is not possible to overfly the large expanses of high-altitude terrain without restrictions and still comply with descent profiles described above.

Oxygen undersupply to body tissue in healthy people is usually attributable to an oxygen-poor environment, which may still have an oxygen content of 21% but is under reduced pressure. Probably the greatest risk of acute oxygen deficiency for an average healthy human is cabin depressurization in an aircraft. If the cabin pressure drops unexpectedly at high flight altitudes, the low partial pressure of oxygen leads to an undersupply of oxygen to body tissue (hypoxia). Hypoxia can cause severe organ damage, possibly even leading to death. One insidious characteristic of hypoxia is that it is not always detected or is detected too late by those affected, so their ability to act is impaired before they can take corrective action. Symptoms of hypoxia range from improper self-assessment, euphoria, fatigue, disorientation to unconsciousness. In aviation, hypoxia is an extremely serious physical condition which can have fatal consequences, most particularly for the crew of an aircraft.

When 100% pure oxygen is supplied to humans, the partial pressure of oxygen is increased five-fold. According to Henry's Law, the partial pressure of a gas over a liquid is proportional to the concentration of the gas (physically) dissolved in this liquid. Thus, when the body receives pure oxygen, the proportion of dissolved oxygen in the blood increases five-fold. However, the gas law does not apply to the oxygen which is chemically bonded to the haemoglobin in red blood cells. Under normal breathing conditions, the oxygen saturation of the blood is already 95-100%. Thus, during ventilation it is mainly the fraction of physically dissolved oxygen that is enriched, and this is correspondingly pressure-dependent. If a human inhales pure oxygen at an atmospheric pressure of 2.5 bar, 20 times the amount of oxygen is dissolved in blood compared to standard conditions. This "systematic hyperbaric oxygenation therapy" is used when low blood oxygen in a patient's body tissue is hindering the healing process, or when oxygen must be supplied as a life-saving measure in emergency cardiovascular or pulmonary situations. However, hyperbaric oxygenation has so far not found wide clinical application, mainly because of the side effects of high oxygen content and excess pressure. The oxygen therapy in intensive-care medicine is one of the main causes of injury due to oxygen intoxication.

The pressure of breathing air is a highly regulating parameter. It can also exert a moderating influence when enriching blood with oxygen. If pure oxygen is used in continuous, supervised ventilation, as in space travel for example, the ambient pressure is throttled considerably, to about 0.3 bar. In this way, the air pressure and therewith the oxygen partial pressure of the supplied respiratory air can be reduced (cf. oxygen partial pressure of 0.21 bar under normal pressure). With continuous ventilation with pure oxygen, the risk of oxygen intoxication is present as early as pressures above said value of 0.3 bar.

Ventilation with pure oxygen can be made possible for various scenarios if the ambient pressure is varied accordingly, but its conflicting characteristics mean that the oxygen cannot be supplied alone in the doses required to counteract oxygen insufficiency without side effects. But it has now been discovered in experiments and trials that inhalation of a gas mixture containing 4±3% carbon dioxide at 10'000 ft flying altitude, 7±5% carbon dioxide, particularly 8±3% carbon dioxide at 15'000 ft flying altitude, 13±3% carbon dioxide at 20'000 ft flying altitude, 16±3% carbon dioxide at 25'000 ft flying altitude and increasing up to 17±5% carbon dioxide, particularly 19±3% carbon dioxide at 30'000 ft flying altitude enables unprecedented improvement to be attained for both physical and mental functional performance in a condition of acute oxygen under-saturation.

If an undersupply of oxygen occurs in the body, the body reacts by accelerating the breathing rate. The increase in the breathing rate causes more oxygen to be inhaled per unit time, but at the same time more carbon dioxide is exhaled. In the body, carbon dioxide is chemically bound as carbonic acid (H2CO3). From the formula below

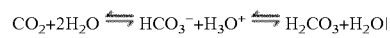
$$CO_2 + 2H_2O \rightleftharpoons HCO_3^- + H_3O^+ \rightleftharpoons H_2CO_3 + H_2O\downarrow$$

the chemical balance indicates that reducing carbon dioxide in the body results in the number of H3O+-ions in the blood to be reduced correspondingly. This causes a shift in the acid-base equilibrium, because the blood becomes increasingly alkaline. In extreme cases, this results in a respiratory alkalosis with symptoms such as muscle cramps, impairment of consciousness, even loss of consciousness. Moreover, the rise in the blood pH-value causes a decrease in the concentration of freely dissolved ionized calcium (hypocalcaemia), leading to hyper-excitability of the musculature and nervous system with spasmodic symptoms. Conversely, an increased concentration of carbon dioxide in the blood shifts the blood pH-value into the acid range. Carbon dioxide-sensitive receptors are located on the vessels of many organs. Depending on the specific organ, the blood vessels either contract or expand under the influence of carbon dioxide. The vessels of the brain expand upon an increase of carbon dioxide concentration. The blood-flow rate increases and with it the amount of oxygen that reaches the cells per unit time. In this way, the body attempts to compensate for the oxygen undersupply, and in particular, to supply the brain with sufficient oxygen for as long as possible. The opposite effect is observed if the body is supplied with oxygen in high doses while reducing the carbon dioxide supply. Hypocapnia, i.e. a low carbon dioxide partial pressure in the arterial blood, leads to contraction of blood vessels in the brain and consequently reduces the blood and oxygen supply. When cabin pressure is lost in an aircraft, an undersupply of oxygen to the body occurs. The body begins to hyperventilate.

Even if a user reaches for the artificial respiration mask relatively quickly, the tendency to hyperventilate is further increased by the stress-inducing circumstances. Hyperventilation accelerates the rate at which carbon dioxide is exhaled. This reduces the level of carbon dioxide in the body. Since the ventilated person moves very little in the situation described, less carbon dioxide is produced by the muscular cells and the effect of carbon dioxide deficiency is accelerated accordingly. For aircraft occupants who are restricted to their seats for most of the time, and most particularly in emergency situations, this limitation of mobility may have severe consequences, because the body then produces less carbon dioxide. Not least because of this fact, a rapid descent to a safe flight altitude is essential for survival.

If a dosed, pressure-dependent quantity of carbon dioxide is added to the breathing gas as mentioned in the introduction, the effects described in the section above can be diminished. But the quantity of carbon dioxide may also be coupled to other conditions or specified in other ways. As the active supply of carbon dioxide to the body relaxes blood vessels in the brain, the oxygen supply to the body tissue takes place in a more efficient manner, while at the same time the amount of oxygen is reduced. Oxygen is then reabsorbed more quickly and to a greater extent, and so provided to the tissue and cells. The gas mixture for enabling ventilation in emergency situations increases the bioavailability of oxygen, in particular oral bioavailability, because by virtue of its mode of action carbon dioxide in precisely measured doses functions as a bioenhancer. Finally, because of the gas mixture the body is kept at a physiological level of carbon dioxide with just a partial dose of oxygen and over a substantially longer period, which provides significant advantages, particularly in the case of depressurization of aircraft cabins.

Aeromedical experiments have demonstrated that by inhalation of air enriched with carbon dioxide aviation standard values can be attained: 84% oxygen saturation of the blood is prescribed for a short bridging time of not more than one minute, and 90% for a bridging time lasting more than one minute. Test persons were administered the amount of carbon dioxide required to maintain the carbon dioxide level in the blood at a physiological carbon dioxide partial pressure of 40 mmHg at various density altitudes. The respiratory air was enriched with 8% carbon dioxide for density altitude 15,000 ft, 11% carbon dioxide for 20,000 ft, and 16.5% carbon dioxide for 30,000 ft. This enrichment was at the expense of nitrogen. Consequently, the gas mixtures for synthesized breathing air were composed as follows:

At 15,000 ft density altitude: 21% oxygen, 8% carbon dioxide, 71% nitrogen

At 30,000 ft density altitude: 21% oxygen, 16.5% carbon dioxide, 62.5% nitrogen

Each test person had to undergo two simulated emergency descent profiles from an altitude of 37,000 ft to 10,000 ft, the descent corresponding to the profiles specified by the ICAO. During the one descent, the test persons inhaled 100% pure oxygen as the hitherto standard in a cabin pressure loss scenario, and during the second descent a gas mixture with carbon dioxide enrichment as described above. The experiment was structured in a randomized, double-blind protocol. Neither observers nor test persons knew which gas mixture would be supplied in which descent. During a descent from 40'000 ft to 21'000 ft following a loss of pressure, a physiological blood oxygen saturation may be achieved at 40'000 ft with a ventilation gas mixture consisting of X % oxygen and Y % carbon dioxide and possibly Z % air, particularly 80% oxygen and 15% carbon dioxide and 5% air, and at 21'000 ft with air that is enriched with 12% carbon dioxide in favour of the nitrogen, wherein the air in this case consists of 21% oxygen, 78% nitrogen and 1% residual gases. From this, the general advantage may be derived that oxygen only has to be mixed with carbon dioxide and possibly air initially, while depending on the altitude reached only a mixture of air enriched with carbon dioxide is sufficient.

The results indicate that the following decisive advantages can be obtained by preparing a corresponding ventilation gas mixture:

1. The amount of oxygen that needs to be carried in an aircraft can be reduced.
2. Based on the adapted drift-down procedures, more direct flight routes can be flown, thus saving very substantial costs and time.
3. Since—as a consequence of the above—less onboard fuel is needed, the cargo capacity of the aircraft is increased.
4. Owing to the reduced fuel consumption the environmental impact is mitigated.

A particularly elegant aspect of the overall concept of the apparatus, the ventilation mask, the method, and its use in additive dosing of carbon dioxide consists in that a user himself produces at least part of the carbon dioxide required. During normal inhalation under normal pressure, respiratory air consists of approx. 78% nitrogen, approx. 21% oxygen and approx. 1% residual gases. In exhaled air, measurements show approx. 78% nitrogen, 16% oxygen, 4% carbon dioxide and approx. 2% residual gases. This carbon dioxide as well as the oxygen can be recovered. During the dosed addition of carbon dioxide to the gas mixture, a portion of the carbon dioxide and the oxygen may thus be supplied directly by the ventilated person him/herself and is then inhaled again by him/her while the rest is added synthetically, wherein the higher the density altitude, the more carbon dioxide needs to be dosed additively at the expense of nitrogen.

The use for preoxygenation prior to intubation is not related to a flying operation, but it is still predicated on the same basic idea for preparing a ventilation gas mixture, particularly with regard to the consequences of oxygen saturation and the effect of additive dosing with carbon dioxide. In this context, it should also be stated unequivocally that conversely the further uses are not limited exclusively to the area of flying operations.

As mentioned before, relatively small quantities of carbon dioxide are added to the ventilation air, in order to allow the human body to better absorb and utilise the ambient oxygen, especially when operating at high altitude. Mixing 8-12% carbon dioxide with ambient air at altitudes of approximately 22,000 ft significantly reduces the effects of hypoxia to acceptable levels.

There are two main methods by which this ventilation gas mixture, with additional carbon dioxide, can be produced. The first method of producing the ventilation gas requires carbon dioxide to be mixed into the gas in lieu of nitrogen in order to preserve the relative percentage of oxygen within the breathed air. Failure to do this (i.e. remove nitrogen after carbon dioxide has been added to ambient air) would result in the partial pressure of oxygen to be further reduced from an already reduced level, especially at altitude, and could therefore contribute to the risk of hypoxia. Table 2 below illustrates the different carbon dioxide quantities, at 21,000 ft, and identifies the percentage decrease in oxygen that occurs, and the corresponding nitrogen removal that would be required to regain the 20.95% oxygen.

TABLE 2

Potential gas mix cases based upon examples of 8, 10 and 12% carbon dioxide levels

|  | Nominal carbon dioxide | 8% carbon dioxide | 10% carbon dioxide | 12% carbon dioxide |
|---|---|---|---|---|
| oxygen | 20.95 | 20.95 | 20.95 | 20.95 |
| nitrogen | 78.08 | 70.08 | 68.08 | 66.08 |
| carbon dioxide | 0.04 | 8.00 | 10.00 | 12.00 |
| Other | 0.93 | 0.97 | 0.97 | 0.97 |
| % nitrogen to be removed (by volume of total air mass) | N/A | 1.75 | 2.19 | 2.63 |
| % oxygen to be added (by volume of total air mass) | N/A | 1.68 | 2.10 | 2.51 |

The second method of producing the ventilation gas, whilst maintaining 20.95% oxygen, requires adding small quantities of oxygen or removing a small quantity of nitrogen to the air mixture which will be mixed with the additional carbon dioxide in order to allow oxygen to become a greater relative proportion of the air volume. This is important because when the carbon dioxide is added it displaces some of the oxygen and some of the nitrogen and so this ensures that the overall resultant oxygen is maintained at substantially 20.95% by volume. Table 2 above illustrates the percentages of oxygen required in order to achieve the same results.

It should be noted that only one of the above two methods is required, that is either the removal of nitrogen, for example according to the quantities given in Table 2, or the addition of oxygen, for example according to the quantities given in Table 2. As will be appreciated, any other percentages, other than those given in Table 2, may also be used when removing nitrogen or adding oxygen, as long as overall 20.95% oxygen is achieved. In some cases, it may be acceptable for the ventilation gas mixture to have relative quantities of carbon dioxide, oxygen, and nitrogen which lie outside these parameters (that is, 20.95% oxygen is not achieved) such as where a reduced human performance via some mild hypoxia is an acceptable state for the individual to be in temporarily. Examples of such situations may include operating at lower altitudes where the hypoxia risks are lessened or operating below ground level (e.g. mining), where oxygen is reduced to minimise explosion/fire risk, but the partial pressure of oxygen is increased.

There are therefore three different types of ventilation gas mixtures which can be created, where "type" is used to refer to the amount of oxygen gas present in the ventilation gas mixture, as follows:
1. A gas mixture comprising 20.95% oxygen (which may be referred to as a "normal" type gas mixture);
2. A gas mixture comprising less than 20.95% oxygen (which may be referred to as a "reduced" type gas mixture), and accepting a reduced blood oxygen saturation level, although still enhanced (as a result of the additional carbon dioxide) relative to simply breathing normal i.e. ambient air (which in this case is air comprising about 21% oxygen and 0.04% carbon dioxide);
3. A gas mixture comprising greater than 20.95% oxygen (which may be referred to as an "enhanced" type gas mixture) in order to achieve an even better human response, compared to breathing ambient air or a normal type gas mixture comprising 20.95% oxygen.

It should be noted that throughout this disclosure, an ideal percentage of oxygen in the ventilation gas mixture has been stated as 20.95%. In practice, the amount of oxygen in the ventilation gas mixture will typically be in the range 18%-24%. Preferably the amount of oxygen is at least 21%. This corresponds to additional carbon dioxide in the range 10%-16%, preferably 12%.

The following description will explain how exhaled carbon dioxide from the user's breath can be re-used and mixed with ambient air from the cabin, to form carbon dioxide enriched air, which is used to make the ventilation gas mixture. This ventilation gas mixture is then passed to the ventilation mask to be inhaled by the user. All the of the ventilation mask configurations described previously may be used with the ventilation gas mixture produced by any of the following methods.

As mentioned earlier, in some cases the carbon dioxide enriched air may have some of the nitrogen removed or the carbon dioxide enriched air may be supplemented with a small quantity of oxygen, in order to further improve the effectiveness of the system. The processes by which this is achieved will be explained in more detail later.

In general, the captured carbon dioxide from the exhaled breath of a user is recycled back into the ambient air at quantities between 0% and 16% carbon dioxide by volume to form the ventilation gas mixture. The amount of carbon dioxide which is recycled back into the ambient air depends on the altitude at which the ventilation gas is required to be used at, the partial pressure of oxygen, and system performance requirements (for example, manufacturing limits of the system components and physiological requirements of the human body e.g. how much carbon dioxide is needed and for what duration in order to first improve oxygen saturation and then maintain a satisfactory level), as has been explained earlier.

Rather than supplying the carbon dioxide into a respiration mask from a long duration storage system (e.g. a carbon dioxide chemical generator or a pressurised carbon dioxide canister), as is done with current systems, the system described herein captures and uses the carbon dioxide from the mask wearer's own exhaled breath.

The carbon dioxide is captured from the exhaled air using a sorbent material, from which the carbon dioxide is then extracted and released back to the mask wearer to be re-inhaled. The method by which carbon dioxide is captured and recycled makes use of molecular adsorption using either Temperature Swing Adsorption (TSA) or Pressure Swing Adsorption (PSA). Generally speaking, TSA is the act of heating and cooling a sorbent material in order to capture and release gas. The process of heating and cooling using an electric heater is referred to as Electric Swing Adsorption (ESA). Thus, any references to TSA include ESA, and via versa. These extraction techniques will be described in more detail below, with reference to FIGS. 15 and 16 which illustrate the general processes for PSA or TSA respectively.

Figure 15:
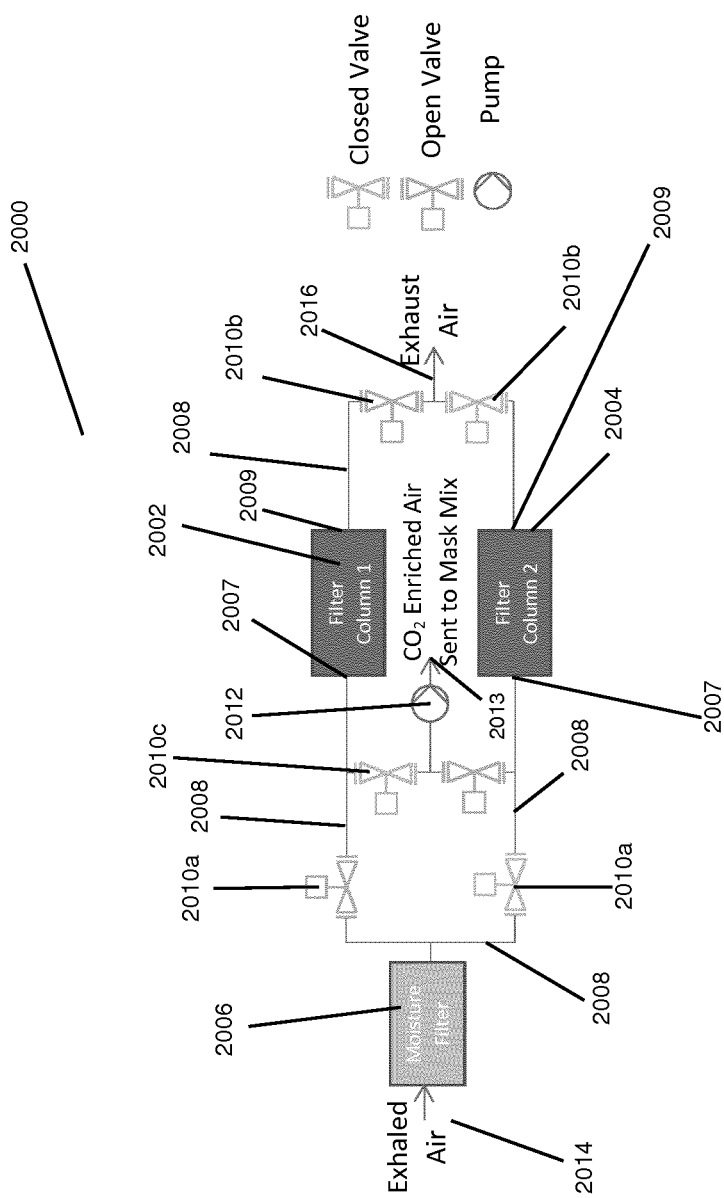
FIG. 15: a schematic representation of a pressure swing adsorption system for carbon dioxide capture.

FIG. 15 shows an example PSA system 2000 which is in the form of a dual filter system comprising an air inlet 2014 via which exhaled air can enter the system 2000, an exhaust outlet 2016 via which air can be exhausted from the system 2000, and two gas reservoirs in the form of filters, namely a first filter 2002 and a second filter 2004, located between the air inlet 2014 and the exhaust outlet 2016. The system 2000 also includes a moisture filter 2006, located upstream of both the first and second filters 2002, 2004 and in fluid communication with both filters 2002, 2004. By upstream we mean that air entering the system 2000 flows through the moisture filter 2006 before it flows through either of the first or second filters 2002, 2004. The moisture filter is therefore positioned in a flow path between the air inlet and the filters 2002, 2004. The PSA system 2000 comprises a number of gas feeds 2008 which connect the various components of the system 2000 together so that air can flow between the components through the system 2000. The gas feeds 2008 therefore ensure that the individual components of the PSA system 2000 are in fluid communication with each other.

The system 2000 further comprises a number of valves 2010, positioned at various locations along the gas feeds 2008 (as will be described in more detail later) in order to control the flow of air through the gas feeds 2008 and into, or out of, the various components such as the filters 2002, 2004.

A pump 2012 is also connected to the PSA system 2000 using a gas feed 2008 and is located downstream of the moisture filter 2006. The pump 2012 is in the form of a vacuum pump which acts to draw air out of the first and second filters 2002, 2004 by decreasing the pressure in the filters 2002, 2004 and so the pump 2012 is in fluid communication with the rest of the system components. In general, exhaled air is pushed into the system 2000 via the air inlet 2014, passes through the system, in particular the filters 2002, 2004 via the gas feeds 2008, and either exits the system via an exhaust outlet 2016 or via a mixture port 2013.

Each filter 2002, 2004 has an input port 2007 and an output port 2009, which allow air to enter and leave the filter respectively. Air flow into and out of these ports is controlled by a set of valves which are able to switch between an open position (in which gas can flow through the valve) and a closed position (in which gas cannot flow through the valve). Each filter 2002, 2004 further comprises a housing and filter material, wherein the filter material is tightly sealed within the housing. Typically, the filer material resides within an internal cavity created by the housing. However, in some cases the filter material itself may form at least part of the housing structure. It is important that the housing can be tightly sealed so that a pressure decrease (i.e. a vacuum, or partial vacuum), can be achieved within the internal cavity inside the housing, where the filter material is located, by the pump 2012. Since the PSA system 2000 operates using pressure gradients, if the internal cavity inside the housing cannot be suitably sealed the system 2000 will not operate effectively or at all in some cases. In this context, sealed means that fluids, in particular gases, cannot flow into or out of the filter, except via the input 2007 and output 2009 ports when the valves 2010 are configured in the "open position to allow fluid to flow through the filter. The housing is therefore hermetically sealed.

The housing can be made from any suitable material which can effectively be sealed and withstand the typical pressures experienced by the system.

The filter material within the housing is a sorbent material having a porous structure or sponge-like structure which behaves like a molecular sieve. This material structure allows molecules having a size which is greater than the size of the pores in the material to collect within the material (that is, into or out of the material), whilst allowing molecules having a size which is less than the size of the pores to pass through the material (that is, into or out of the material). The sorbent material therefore behaves like a partially selective filter. The material can be chosen to be selective towards a particular molecule of interest. Thus, in terms of filter material, any suitable selectively sorbent material for carbon dioxide can be used, such as, but not limited to, Zeolite 13X or a bespoke manufactured Metal Organic Framework (MOF) material.

Each of the first and second filters 2002, 2004 has a plurality of valves 2010, in particular three valves, associated with it. The first valve 2010a is positioned between the moisture filter 2006 and the filter 2002, 2004 i.e. upstream of the filter and the sorbent material. The first valve 2010a is therefore positioned in a flow path between the moisture filter 2006 and the filter 2002, 2004. This first valve 2010a controls the flow of gas into the sorbent material. The second valve 2010b is positioned between the filter 2002, 2004 and the exhaust outlet 2016 leading to the surroundings i.e. downstream of the filter and the sorbent material. The second valve 2010b is therefore positioned in a flow path between the filter 2002, 2004 and the exhaust outlet 2016. This second valve 2010b controls the flow of waste gas through the exhaust outlet 2016 and back into the surroundings. The third valve 2010c is positioned between the filter 2002, 2004 and the pump 2012. This third valve 2010c controls the flow of gas (which will generally be carbon dioxide, however in some cases small quantities of nitrogen and/or oxygen may also be present) extracted from the sorbent material into the gas mixing device 3, where the ventilation gas mixture is produced.

These valves 2010 can be electrically or mechanically actuated, for example controlled by either a fixed mechanical or electrical timer. In some cases the valves 2010 can be controlled by a microprocessor based upon measured carbon dioxide levels from a sensor within the system 2000. In this case, when the measured carbon dioxide level within the sorbent material reaches an upper threshold level (for example corresponding to either a maximum amount of carbon dioxide that can be captured by the filter 2002 or any other quantity of carbon dioxide required), the first and second valves 2010a, 2010b are shut and the third valve 2010c is opened in order to allow the captured and stored carbon dioxide to be extracted using the pump 2012. When the measured carbon dioxide level within the sorbent material reaches a lower threshold level (for example corresponding to an empty filter 2002 containing none or very little carbon dioxide), or alternatively based on pre-determined timings, the third valve 2010c can be shut and the first valve 2010a re-opened in order to allow further carbon dioxide to be captured and stored by the sorbent material. Any gas that passes straight through the filter 2002 is exhausted to the surroundings, i.e. the cabin, via the second valve 2010b and the exhaust outlet 2016.

In order to capture carbon dioxide from the exhaled air using PSA, the exhaled air breathed out by a person is passed directly into the PSA system via the air inlet 2014 through the action of the person breathing out (exhaling), this exhaled air pressure may be increased by use of a pump. By "directly" we mean that a person exhales into a gas feed which supplies air to the PSA air inlet 2014. It is also possible to use an intermediate collection area (e.g. a storage bag) which temporarily stores the exhaled air before supplying it to the air inlet 2014. In this case, a pump is required to generate the required positive pressure need to push the stored exhaled air from the intermediate collection area into the filter 2002 under pressure. The pump is located downstream of the intermediate collection area but upstream of the moisture filter 2006. The exhaled air therefore passes through the pump before it passes through the moisture filter 2006. This configuration (having an intermediate collection area and pump) would increase the adsorbent performance of the filter as the increased pressure provided by the pump, compared to the positive pressure provided by a person exhaling, would help to force the carbon dioxide molecules into the adsorbent filter material. Using this configuration may include a restrictor valve to be located within the exhaust outlet 2016 so that the pump can sufficiently increase the pressure within the system 2000. This restrictor valve is not needed when a person is providing the positive pressure because it would be uncomfortable for a person to exhale into a system against the action of the restrictor valve and the person may not be able to provide a sufficient pushing force to force the exhaled air through the entire system 2000.

The exhaled air is then passed through the sorbent material which is contained within the filter 2002. As discussed earlier, the air is passed through the PSA system 2000 under pressure, either as a result of a pump which creates a pressure gradient between the air inside the system and the ambient air in the cabin or as a result of a person exhaling and generating the required positive pressure.

During operation of the PSA system 2000, the ambient air enters the PSA system 2000 via the air inlet 2014 and is passed initially through the moisture filter 2006 (which can be in the form of a condenser, filter, or adsorbent system, or any other suitable method for removing moisture). The action of the user exhaling through the system 2000 produces enough positive pressure to push the exhaled air into the system 2000 and through the moisture filter 2006. However, in some cases, the system 2000 comprises an additional pump which pushes the exhaled air through the moisture filter 2006.

The moisture filter 2006 is required in order to remove excess moisture from the ambient air before the air passes through the filter 2002 and the sorbent material. This is because the sorbent material, as well as capturing carbon dioxide, will also capture some water molecules and other gases present in the exhaled air. Whilst the sorbent material is selective, meaning that it has a preference for adsorbing some molecules over others (for example, carbon dioxide in this case), it will also adsorb other molecules that are not small enough to pass through the sorbent material (for example water in this case). If the majority of the water molecules are not removed before the air passes through the filter 2002, the filter 2002 is likely to capture large quantities of water molecules alongside the carbon dioxide, resulting in a lower quantity of carbon dioxide being captured and stored by the filter 2002. Thus, in order to improve the effectiveness of the filter 2002 in capturing carbon dioxide, water is initially removed from the air. In some cases, failure to remove moisture from the exhaled air would block the sorbent material and stop the filter working.

After the exhaled air has been passed through the moisture filter 2006, it then passes through the first valve 2010a and into the selective sorbent material contained within the first filter 2002. This is again achieved under the action of the user exhaling creating a enough positive pressure to force the exhaled air through the first filter 2002, but in some cases a pump is used to actively force i.e. push the air through the first filter 2002, as mentioned earlier.

The selective sorbent material stores relatively large quantities of the carbon dioxide from the exhaled air. As will be appreciated, the actual amount of carbon dioxide stored will depend on the choice of sorbent material. For example, sorbent material made of Zeolite 13X can adsorb 2.25 mmoljg carbon dioxide (i.e. 2.25 milli-moles of gas per gram of adsorbent). It should be noted that although mmol/g is the most common unit of measurement, this could also be represented as 0.099 g carbon dioxide per gram of Zeolite.

As the exhaled air passes through the filter 2002, the sorbent material captures carbon dioxide from the exhaled air and retains it within the structure of the sorbent material. The remaining air, including any remaining carbon dioxide left in the air, that has not been captured by the sorbent material continues to pass through the filter 2002 and is then exhausted out of the exhaust outlet 2016 to the surroundings as waste gas, via the second valve 2010b which is a pressure release valve. Once the first filter 2002 has captured a maximal quantity of carbon dioxide, any air within the system 2000 or any new air entering the system 2000 continues to pass straight through the filter 2002 and out of the system 2000 via the exhaust outlet 2016. Generally, a maximal quantity of carbon dioxide means that the sorbent material is unable to adsorb any further carbon dioxide molecules. The filter 2002 may therefore be referred to as being full. The actual quantity of carbon dioxide gas, in terms of volume, that the filter 2002 can capture before it reaches a full state depends on the sorbent material chosen, as different materials can capture and store different quantities of gas, as well as on the temperature and the pressure at which the carbon dioxide is introduced into the filter 2002.

In some cases, a "full" filter corresponds to a filter having less than 100% carbon dioxide captured within the sorbent material. For example the filter 2002 may be determined to be full when the sorbent material comprises 80% carbon dioxide gas. This may occur when the required mixture of gases has been reached and no further carbon dioxide is required. For example, this may occur if a system is using pre-determined timings so control when and for how long each filter is either capturing carbon dioxide or releasing carbon dioxide. Alternatively, this point can be detected using a number of sensors which can detect the proportion of oxygen and carbon dioxide present in a particular gas sample by determining the partial pressures of oxygen and carbon dioxide. These sensors could be positioned within the filters themselves, or at the exhaust outlet 2016 from the whole system, or in a ventilation gas mask. Alternatively there may be no sensors at all, and the system may rely on pre-determined timings based upon the physical characteristics of the system, for example how long it typically takes a filter to reach a full state which can be determined using lab experiments or estimated. Since the amount of carbon dioxide required in the ventilation gas mixture is dependent on the altitude, the amount of carbon dioxide which corresponds to a full filter also varies with altitude.

In order to extract the stored carbon dioxide from the first filter 2002, the pump 2012, which is in the form of a vacuum pump, is used to create a partial vacuum within the filter 2002. The pump 2012 therefore sets up a pressure gradient so that the captured carbon dioxide is drawn from the relatively higher pressure environment inside the filter housing to the lower pressure gas feed via the third valve 2010c.

In some cases the valves could be in other combinations. For example, it could be possible to replace 2010b with a non-return valve under some design conditions. Also, it may be possible to have valves 2010a and 2010c in a combined two (or more) port valves with their opposite valves on the secondary reservoir.

In some examples, the gas extraction process (in particular, the point in time at which the first filter 2002 starts to release the captured carbon dioxide) is determined by at least one sensor configured to measure the oxygen saturation levels of the air breathed by the user and send these measurements to a processors to processing. This oxygen sensor is therefore located in a gas feed that is close to the user's mouth.

Once is has been determined, by the processors, that the oxygen saturation level has fallen below a minimum threshold level, the processor is configured to activate the pump 2012 and initiate the carbon dioxide extraction process. The minimum threshold level, and thus the amount of carbon dioxide required, depends on altitude. Thus, the processor determines whether the oxygen saturation level is acceptable for a particular altitude and, if not, triggers the extraction process accordingly. The extracted carbon dioxide as fed into the gas mixing device 3 via a gas feed 2008 and a gas inlet 2001. Here, the extracted carbon dioxide is then mixed with other gases (namely oxygen, nitrogen, and ambient air, either individually or in combination) which have been supplied to and entered the gas mixing device 3 via a number of other gas inlets to generate the correct air mixture for ventilation. The ventilation gas mixture is then fed from the gas mixing device 3 into the ventilation mask via another gas feed 2010 and a gas mixture outlet 2003. The user then breaths in the carbon dioxide enhanced air via the ventilation mask.

Whilst this disclosure has described the use of sensors to determine and control the point in time at which the function of each filter is switched between capturing and releasing, it would also be possible to design and configure a system which uses at least one timer to control the function of the filters. The timer would control the operation of the valves 2010 so that the air flow is directed through the system 2002 and alternately between the two filters 2002, 2004, depending on which combination of valves are open and closed.

Thus, this description is intended to cover systems in which the function of the filters is controlled using a timer, by sensors (which may be in the filter, in the supply/exhaust or output lines, or in a mask, or a microprocessor (or similar logic circuit) which may be employed to control the operation of the system based upon timings, and/or measured oxygen either within or exiting the filter system.

As was mentioned previously, with reference to FIG. 8, the ventilation mask 500 may include a second reservoir 504' having a filter 5041'. This filter allows components from the exhaled air to be made available to the second reservoir 504' so that the components can form part of the ventilation gas mixture. The components extracted from the exhaled air can be stored in the second reservoir 504', ready for discharge and usage, as required. In this case, the component is carbon dioxide. Thus, in some cases, this second reservoir and filter may be one of the filters 2002, 2004 that forms part of the PSA system 2000. Alternatively, the PSA system 2000 and ventilation mask are separate components and in this case the carbon dioxide is supplied from the PSA system 2000 and fed into the ventilation mask.

Figure 16:
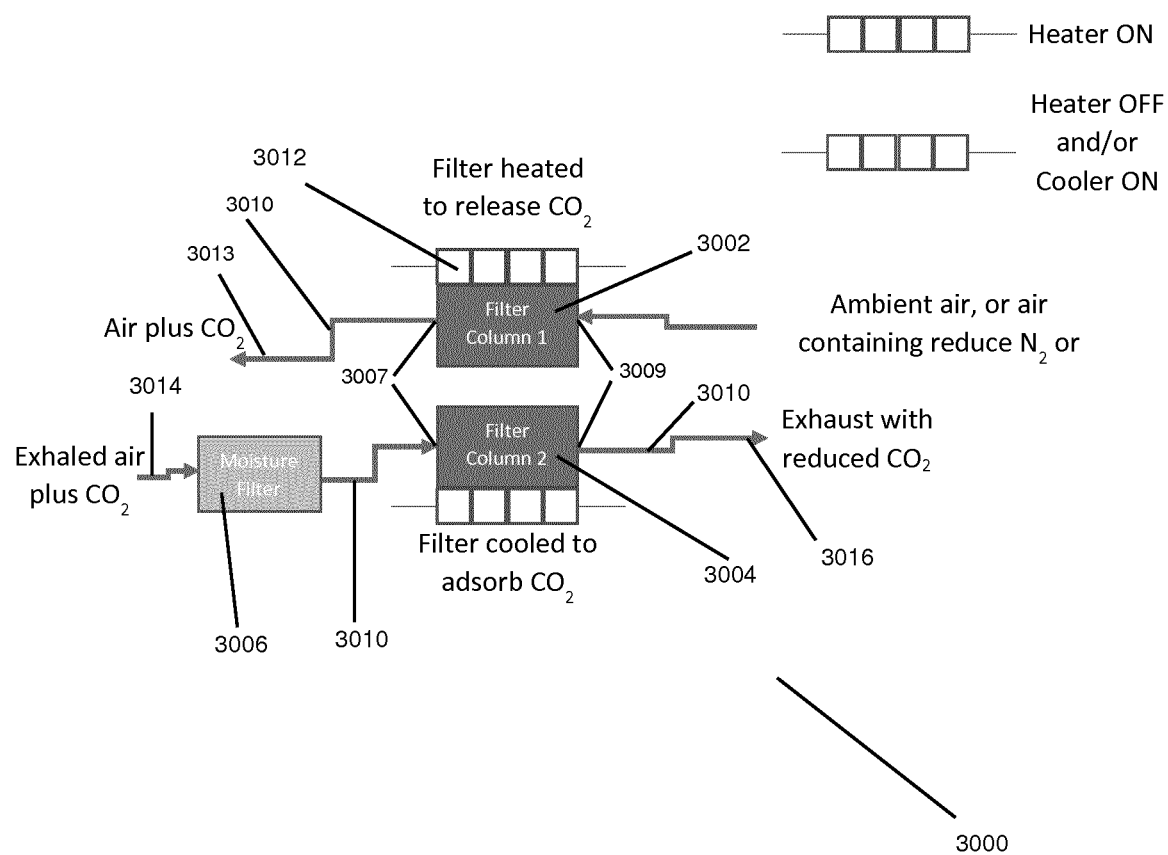
FIG. 16: a schematic representation of a temperature swing adsorption system for carbon dioxide capture.

FIG. 16 shows an example TSA system 3000 which is in the form of a dual filter system comprising an air inlet 3014 via which exhaled air can enter the system 3000, an exhaust outlet 3016 via which air can be exhausted from the system 3000, and two TSA gas reservoirs in the form of filters, namely a first TSA filter 3002 and a second TSA filter 3004 located between the air inlet 3014 and the exhaust outlet 3016. The TSA system also includes a TSA moisture filter 3006, located upstream of both the first and second TSA filters 3002, 3004 and in fluid communication with both TSA filters 3002, 3004. The moisture filter 3006 is therefore positioned in a flow path between the air inlet 3014 and the filters 3002, 3004. The TSA system 3000 further comprises a number of gas feeds 3010 which connect the various components of the TSA system 3000 together so that air can flow between the components through the TSA system 3000. The gas feeds 3010 therefore ensure that the individual components of the TSA system 3000 are in fluid communication with each other.

In general, exhaled air is pushed into the system via the air inlet 3014, passes through the filters 3002, 3004 in the system 3000, and either exits the system via the exhaust outlet 3016 or via a mixture port 3013.

As with the PSA system 2000, each TSA filter 3002, 3004 has an input port 3007 and an output port 3009, which allow air to enter and leave the filter respectively.

Air flow into and out of these ports is controlled by a set of valves 3010 which are able to switch between an open position (in which gas can flow through the valve) and a closed position (in which gas cannot flow through the valve). Each filter 3002, 3004 further comprises a housing and filter material, the filter material being substantially sealed within the housing. Typically, the filer material resides within an internal cavity created by the housing but in some examples the filter material itself may form at least part of the housing structure. Again, it is important that the housing is sealed so that the internal cavity inside the housing, where the filter material is typically located, can either be heated or cooled, whereby obtaining and maintaining a specific low temperature range allows gas adsorption, and obtaining and maintaining a specific high range allows gas de-adsorption. The TSA system 3000 works based on the adsorbent and adsorbent characteristics of the sorbent material, and so if the temperature of the internal cavity and sorbent material contained inside the housing cannot be suitably controlled, the system 3000 will not operate effectively or at all in some cases. In some developments in order to help control and maintain the desired temperature of the filter, mechanisms such as sealing, insulating, or heat shielding from other components of the TSA system can be incorporated.

The housing can be made from any suitable material which can effectively be sealed to maintain and withstand the typical temperatures experienced by the TSA system 3000.

TSA works in a very similar way to PSA, but instead of using a pressure gradient to capture and release the carbon dioxide, a temperature gradient is used. As before, the filter material within the housing is a sorbent material, chosen to be selectively sorbent for carbon dioxide. Any type of suitable selectively sorbent material may be used, such as, but not limited to, Zeolite 13X or a bespoke manufacture Metal Organic Framework (MOF) material. For both TSA and PSA the same sorbent material can be used. However, different sorbent materials could also be used, i.e. a first material for TSA and a different second material for PSA.

Generally, in order to capture carbon dioxide from the exhaled air using TSA, the exhaled air breathed out by a person is passed directly into the TSA system via the air inlet 3014 through the action of the person breathing out (exhaling). As before "directly" in this context generally means that a person exhales into a gas feed which supplies air to the TSA air inlet 3014, this exhaled air pressure may be increased by use of a pump. However, it is also possible to use an intermediate collection area (e.g. a storage bag) which temporarily stores the exhaled air before supplying it to the air inlet 3014. If an intermediate collection area is used then a pump is required to generate the required positive pressure need to push the stored exhaled air from the intermediate collection area into the filter 3002. The pump is located downstream of the intermediate collection area but upstream of the moisture filter 3006 and so the exhaled air passes through the pump before it passes through the moisture filter 3006. This configuration (having an intermediate collection area and pump) increases the adsorbent performance of the filter 3002 because the increased pressure provided by the pump, compared to the positive pressure provided by a person exhaling, would help to force the carbon dioxide molecules into the adsorbent filter material. This configuration may include the use of a restrictor valve, located within the exhaust outlet 3016, so that the pump can sufficiently increase the pressure within the system 3000 in order to force the air through. It should be noted that the restrictor valve is not needed in configurations when a person is providing the positive pressure because it would be uncomfortable for a person to exhale into a system against the action of the restrictor valve. Additionally, the person may not be able to provide a sufficient pushing force to force the exhaled air through the entire system 3000.

The exhaled air is then passed through the sorbent material which is contained within the filter 3002. The TSA filter 3002 is cooled to capture carbon dioxide and then subsequently heated to release the carbon dioxide.

During operation of the TSA system 3000, the exhaled air enters the TSA system 3000 via the air inlet 3014 and is first passed through the moisture filter 3006 (which may be a condenser, filter, adsorbent system, or any other suitable method for removing moisture), in order to remove excess moisture from the exhaled air, as explained previously in the context of the PSA system 2000. The action of the user exhaling through the system 3000 produces enough positive pressure to force the exhaled air into the system 3000 and through the moisture filter 3006. However, in some cases a pump can be used to force the exhaled air through the moisture filter 3006, as outlined above.

After the exhaled air has passed through the moisture filter 3006, it then passes into the selective sorbent material inside the first TSA filter 3002. This is again in general achieved under the action of the user exhaling which forces the exhaled air through the first filter 3002, but a pump may be used to actively push exhaled air through the first filter 3002, as already mentioned. Unlike PSA, the sorbent material used for TSA is cooled using a temperature control means 3012, which in this example is in the form of a Peltier. The Peltier is able to perform both heating and cooling functions and so can be used as a temperature controller.

In the example shown in FIG. 16, the temperature control means 3012 is located next to (either directly next to or slightly spaced apart from) the first filter 3002 so that it can adjust and control the temperature of the sorbent material within the filter 3002. In other examples, not shown, the temperature control means may comprise part of the filter, rather than form a separate component, for example Zeolite 13X powder 3D printed directly onto a heater matrix within the filter 3002.

The temperature control means 3012 adjusts the temperature of the filter housing which in turn adjusts the temperature of the internal cavity within the housing. This has the effect of adjusting the temperature of the sorbent material. In the example shown in FIG. 16, the temperature control means 3012 reduces the temperature of the sorbent material so that it is suitable for the sorbent material to adsorb the selective gas. The temperature control means 3012 is therefore used to place the sorbent material in a cooled state. Typically, a cooled state corresponds to an absolute temperature of 30 degrees or less, which is sufficient for the sorbent material to adsorb carbon dioxide. However, this temperature changes depending upon the specific sorbent material used and may be higher than 30 degrees. In some configurations, the temperature control means 3012 is connected to a computer system which controls the temperature to which the sorbent material should be cooled or heated to. In other configurations a computer system is not required and it would also be possible to cool the sorbent material in an "open loop" uncontrolled manner. In terms of heating, the TSA system might comprise a simple analogue circuit that is configured to measure the temperature of the filter 3002 and turn a heating element on/off. This could also be achieved by a computer or microprocessor. In the cooled state, this selective sorbent material captures and stores relatively large quantities of the carbon dioxide. As discussed with reference to PSA, the actual amount of carbon dioxide stored will depend on the choice of sorbent material used. For example, Zeolite 13X can adsorb 2.25 mmol|g carbon dioxide.

As the exhaled air passes through the TSA filter 3002, the sorbent material captures carbon dioxide from the exhaled air and retains it within the structure of the sorbent material. The remaining air, including any remaining carbon dioxide left in the air, that has not been captured by the sorbent material or any new air that enters the system 3000 continues to pass through the filter 3002 and is then exhausted to the ambient air in the surroundings as waste gas via the exhaust outlet 3016.

Once the first TSA filter 3002 has captured a maximal quantity of carbon dioxide, and so can be considered full, any air within the TSA system 3000 continues to pass straight through the TSA filter 3002 and out of the TSA system 3000 via the exhaust outlet 3016. As mentioned in relation to the PSA system 2000, the actual quantity of carbon dioxide gas which corresponds to a maximal quantity depends on the sorbent material chosen.

In some configurations and situations, the TSA filter 3002 may enters a resting state in which it is storing the captured gas rather than capturing or releasing. The TSA filter 3002 remains in this state until the captured gas is required to be released from the TSA filter 3002. Whilst in the resting state, the TSA filter 3002 does not need to be actively cooled by the temperature control means 3012. The temperature control means 3012 can therefore be switched off, by the computer system, and the TSA filter 3002 can be left at ambient temperature i.e. cabin temperature. Since the sorbent material within the TSA filter 3002 has already been cooled inside the TSA filter 3002, the TSA filter 3002 will continue to store the captured carbon dioxide without any additional cooling being required. This resting state may also apply to the PSA system.

In order to release, or extract, the carbon dioxide which is stored in the sorbent material, the sorbent material is heated using the temperature control means 3012. The temperature control means 3012 increases the temperature of the sorbent material so that it will be at temperature that is suitable to release the stored gas. This temperature is based upon the physical properties of the adsorbent material, characterised by its adsorption isotherm characteristics. The temperature control means 3012 is therefore used to place the sorbent material in a heated state. Typically, a heated state corresponds to an absolute temperature of 60 degrees or more, which is sufficient for the sorbent material to release carbon dioxide.

The time at which the captured carbon dioxide gas is extracted from the first TSA filter 3002 is determined by at least one sensor configured to measure the oxygen saturation levels of the air breathed by the user and send these measurements to a processor for processing. Once is has been determined, by the processors, that the oxygen saturation level has fallen below a minimum threshold level, the processor is configured to activate the temperature control means 3012 to heat the TSA filter 3002 and initiate the carbon dioxide extraction process.

As with PSA, the release of carbon dioxide may not need to be sensed. Instead it may be determined based on a fixed timing, or measurement of carbon dioxide, or additionally for TSA systems, it may be the temperature of a filter bed which is measured (or a combination of multiple sensors). Thus, this description covers systems controlled using a timer, by sensors (which may be in the filter, in the supply/exhaust or output lines, or in a mask, or a microprocessor (or similar logic circuit) which may be employed to control the operation of the system based upon timings, and/or measured oxygen either within or exiting the filter system.

The extracted carbon dioxide is fed into the gas mixing device 3 via a gas feed 2010 and gas inlet 2001 where it is then mixed with other gases (namely oxygen, nitrogen, and ambient air, either individually or in combination) which have been supplied to the gas mixing device 3 via a number of other gas inlets in order to generate the correct air mixture for ventilation. The ventilation gas mixture is then fed from the gas mixing device 3 into the ventilation mask via another gas feed 3010 and gas mixture outlet 2003. The user then breaths in the carbon dioxide enhanced air via the ventilation mask.

Again, with reference to FIG. 8, the filter 5041' of the second reservoir 504' in the ventilation mask 500, allows carbon dioxide from the exhaled air to be made available to the second reservoir 504' so that it can form part of the ventilation gas mixture. In some cases, the carbon dioxide extracted from the exhaled air is stored in the second reservoir 504', ready for discharge and usage, as required. Thus, in some cases, this second reservoir and filter may be one of the filters 3002, 3004 that forms part of the TSA system 3000. Alternatively, the TSA system 3000 and ventilation mask are separate components and in this case the carbon dioxide is supplied from the TSA system 3000 and fed into the ventilation mask.

The temperature to which the sorbent material is heated and cooled varies depending on the particular choice of sorbent material and its associated material characteristics. This means that the specific temperature associated with the cooled state of the sorbent material is particular to each sorbent material. Generally, an operating temperature range of 25 degrees to 65 degrees is used, the lower end of the range corresponding to the cooled state used for capturing carbon dioxide and the higher end of the range corresponding to the heated state used to releasing carbon dioxide. However, as will be appreciated, other temperature ranges may also be used, depending on the sorbent material chosen and the ambient pressure.

The above description describes heating and cooling using a temperature control means in the form of a Peltier. However, a number of different temperature control means can be used instead to achieve the same heating and cooling functions including, but not limited to refrigerants, thin film heaters, and electrical coils. Furthermore, multiple combinations of heating and cooling can be used simultaneously. In some cases, the temperature control means comprises a separate heater and cooler, rather than a temperature control means which can perform both functions. In other cases, the temperature control means comprises a heating means and cooling can be achieved using the action of the exhaled breath passing through the system (which will generally be at a temperature that is lower than the heated filter), or ambient cooling to bring the temperature of the filter down sufficiently in order to allow adsorption when the heater is switched off.

It should be noted that the present disclosure relates to the concept of using PSA or TSA for capturing carbon dioxide for respiratory re-use, irrespective of the precise TSA or PSA process configuration or specific sorbent material. The PSA and TSA processes for recycling carbon dioxide have been described using a dual, or two, filter system, as shown in FIGS. 15 and 16, in which one filter, for example the first filter 2002, 3002, is adsorbing the carbon dioxide, whilst the other filter, for example the second filter 2004, 3004, is releasing carbon dioxide. However, as will be appreciated, a PSA or TSA filter system having any number of filters may be used instead, such as a single filter system or a multi-filter system comprising more than two filters.

In a single filter system, the single filter will first be used to capture and store the carbon dioxide. Once the single filter has adsorbed its maximal quantity of carbon dioxide, the single filter will then be used to release the captured and stored carbon dioxide. A computer control system, in conjunction with a number of sensors configured to measure the oxygen saturation levels of the air breathed by the user, can be used to switch between a capturing function (in which the gas of interest, here carbon dioxide, in captured and stored in the sorbent material) and a releasing or supplying function (in which the stored gas of interest, here carbon dioxide, is supplied to the gas mixing device), based on the oxygen saturation levels which can be used to indicate demand for ventilation air. In some cases, timers can also be used to switch functions. When timers are used, the filter is switched between capturing and releasing carbon dioxide after a pre-determined period of time rather than based on the oxygen saturation levels of the air breathed by the user.

In multi-filter systems, the additional filters can be connected in series or parallel and the additional filters can be rested or cooled as part of the cycle. When the filters are connected in series, each filter is filled (or emptied) individually one after another with subsequent filters being filled (or emptied) once the previous filter has reached its maximum capacity for carbon dioxide capture (or has been completely depleted of captured carbon dioxide). When the filters are connected in parallel, the system may be arranged such that all the connected filters are filled or emptied simultaneously, rather than one after another. In some multi-filter system, when additional filters are not actively adsorbing or releasing carbon dioxide they may be resting or cooling (cooling only happening in the case of using TSA). By resting, we mean that the filter is in an idle state rather than capturing or releasing carbon dioxide. That is to say, the filter is performing a storage function for the captured carbon dioxide. By cooling, we mean that empty filters in a TSA system that have already had their carbon dioxide extracted from them are cooled, after they have been heated to release to carbon dioxide, in order to prepare these filters for subsequent capture of carbon dioxide. In this case, the filters are actively cooled using the temperature control means 3012 in the TSA system 3000. However in some TSA systems the cooling may be passive, meaning that the filter is gradually allowed to decrease in temperature from its heated state and the temperature control means is not used to cool the filter down. The functions of each filter in a multiple filter system can be controlled based upon electrical or mechanical timers, or an electrical or computer-based control system.

Using multiple filters and an associated system of valves allows for more than one filter to capture carbon dioxide from the exhaled air, whilst the other filter or filters release their captured carbon dioxide to be used for gas mixture production. In multiple filter systems, such as the dual filter systems 2000, 3000 described above, the system cycles between using, for example, a first filter 2002, 3002 and a second filter 2004, 3004 (and any other filters that are present in the system as necessary) by closing and opening the first valves 2010*a* associated with each filter.

For example, in the two filter system described above, one filter (e.g. the first filter) may act as a storage filter for capturing carbon dioxide while the other filter (e.g. the second fitter) may act as a releasing filter for releasing captured carbon dioxide. Once the storage filter is full or the releasing filter is empty (or based upon pre-set timing, the timing function set and controlled by a computer system or simple electronics), the system of valves is used to switch the storage filter into the releasing filter and vice versa. An advantage of this multiple filter system is that there is a continuous supply of carbon dioxide available for producing the ventilation gas mixture. There is no pause or downtime while the storage filter is filling up before it can release the carbon dioxide. This allows carbon dioxide to be readily available on demand. A non-continuous, intermittent supply of carbon dioxide is also acceptable, and in some cases may be preferable over continuous supply.

Although the PSA carbon dioxide capturing system 2000 and TSA carbon dioxide capturing system 3000 have been described separately, in some examples the carbon dioxide capturing system will use both PSA and TSA. This combination system will include the components from each individual PSA system and TSA system that have been described above. Thus a combination system will include the vacuum pump and valves from the PSA system as well as the temperature control means from the TSA system. Using a combination of both PSA and TSA to capture carbon dioxide from exhaled air results in a combination system that is more efficient than using either PSA or TSA alone.

Thus, as will be appreciated, this disclosure also covers differing permutations of valves, pumps, and heaters in order to achieve these configurations as well as combinations of PSA and TSA within the same system and a PSA system where a vacuum is used instead of positive pressure (or a combination of high pressure and vacuum in different parts of the cycle).

As mentioned, in order to maintain suitable levels of oxygen in the carbon dioxide enriched air that is used for ventilation either some of the nitrogen is removed or small amounts of oxygen are added. These processes will now be described.

There are a number of different methods by which the carbon dioxide enriched air can be supplemented with additional oxygen.

A first method uses bottled and pressurised oxygen, in order to deliver metered oxygen to each users' mask, the amount of oxygen delivered depending upon the altitude and the breathing rate of the specific user. In this case, the oxygen bottle could be an individual bottle associated with each user on the aircraft (i.e. one oxygen bottle per user), an individual bottle associated with a plurality of users on the aircraft (i.e. one oxygen bottle for more than one user), or a centralised system comprising one bottle which is able to service all the users (such as passengers and crew) on the whole aircraft (i.e. one bottle per aircraft). This type of system would be able to provide 100% oxygen at 40,000 ft and above, either remaining at 100% oxygen until the aircraft descended to 21,000 ft, or decreasing, preferably linearly decreasing, to nominally 2.51% oxygen at 21,000 ft (and then decreasing, preferably linearly decreasing, to 0% oxygen at 10,000 ft). This system could be a demand system, in which the oxygen demand of users is detected based on the oxygen saturation level of the air breathed by the user, or a continuous flow system in which a continuous supply of oxygen is provided independent of the user's demand. The detection is performed by a pressure sensor which could be located, for example, in the user's ventilation mask, in the gas feed line supplying gas to the mask, or in a pressure regulator. This pressure sensor detects the user inhaling and exhaling (rather than measuring the oxygen saturation level). Based on the detection results, the system then knows to stop the supply of oxygen when the user is exhaling because they don't need it. Additionally, a sensor could measure the oxygen content in the gas or within the user's blood using a sensor positioned on the inside of the mask, and in contact with the skin. Both of these sensors would feed results into a computer or logic device, which would allow the oxygen content to be controlled.

Upon detecting an oxygen saturation level which is below an acceptable threshold level, a valve is opened in order to deliver high pressure oxygen, through a regulator which reduces the pressure of the oxygen, into the user's mask. Alternatively, instead of a demand system, the system could be a continuous flow system in which the required partial pressure of oxygen is continually supplied to the user's ventilation mask, irrespective of the breathing cycle.

A second, alternative method uses a chemical oxygen generator to generate the required additional oxygen, in a similar manner to that used by many existing emergency oxygen systems. In this case, the oxygen generator could be an individual generator associated with each user on the aircraft (i.e. one oxygen generator per user), an individual generator associated with a plurality of users on the aircraft (i.e. one oxygen generator for more than one user), or a centralised system comprising one generator which is able to service all the users (such as passengers and crew) on the whole aircraft (i.e. one generator per aircraft). This generated oxygen is supplied to users in the event of a decompression. Although the system will be able to provide 100% oxygen at 40,000 ft and above, this chemical oxygen generation system will need to be modified to change the oxygen release characteristics such that only very small quantities of oxygen are produced once the aircraft descends to 21,000 ft (nominally following the same oxygen release characteristics as described above with reference to the pressured oxygen method). This modification could be achieved by changing the quantity of chemicals permitted to react as time passes and the altitude of the aircraft decreases, so that smaller and smaller quantities of chemicals interact, and therefore lower volumes of oxygen are generated. Alternatively, since a far lower quantity of oxygen would be required during the initial emergency descent, the unused oxygen could be collected in a holding compensation bag, for later mixing within the ventilation system.

The process by which nitrogen is removed from ambient air, using a filter system, in order to increase the amount of oxygen present in the ambient air, is similar to the process used to capture carbon dioxide from the exhaled air.

Nitrogen can therefore be removed from the ambient air, the process being referred to as nitrogen filtration, using either TSA or PSA as described above. However, in the case of nitrogen removal, the air entering the system is ambient air rather than exhaled air from a user and the captured and removed nitrogen is disposed of rather than recycled and reused elsewhere in the system.

The general process for nitrogen filtration, using PSA and TSA, will now be described, with reference to FIGS. 17 and 18 respectively. As with the carbon dioxide capture and recycling system described above, the following disclosure covers different configurations of filter columns, pumps, valves and heaters that could be used in a TSA or PSA system (or combined TSA and PSA system). Furthermore, the term PSA not only covers positive pressure systems, but also Vacuum Swing adsorption systems, or a mixture of positive and vacuum.

Starting with FIG. 17, an example system configured to carry out the process of nitrogen removal using PSA will be described. As has been explained, PSA works by passing air through a sorbent material contained within a filter. For the process of nitrogen removal, the air entering the PSA system is ambient air from the surroundings. This process is normally achieved under pressure, i.e. under a pressure which is greater than standard atmospheric pressure, in order to obtain very high oxygen purity. However, since the aim of the system is based around providing carbon dioxide to the mask wearer, only small quantities of nitrogen filtering are required in order to rebalance the ventilation air mixture back to substantially 20.95% oxygen.

The filter material used for nitrogen filtration is generally the same type of filter material that is used for carbon dioxide capture. The filter material is therefore a selectively sorbent filter material, being selective towards nitrogen this time rather than carbon dioxide. In terms of filter material, any suitable selective sorbent material can be used, such as, but not limited to, Zeolite 13X, or a bespoke manufacture Metal Organic Framework (MOF) material.

Figure 17:
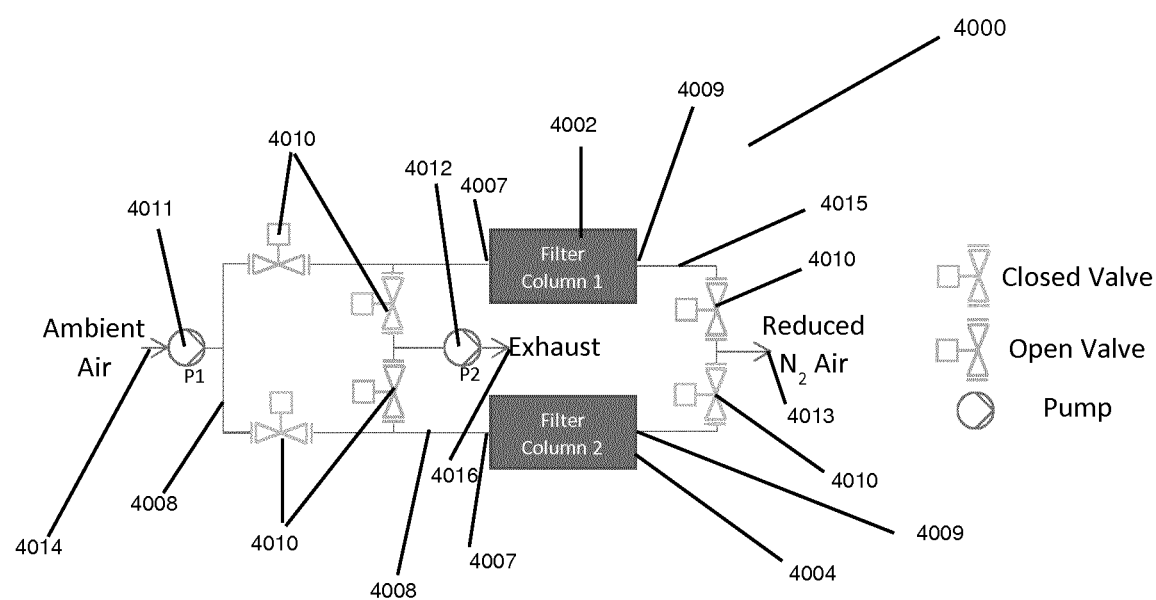
FIG. 17: a schematic representation of a pressure swing adsorption system for nitrogen removal.

The example nitrogen filtration system 4000 shown in FIG. 17 takes the form of a dual filter system comprising an air inlet 4014 via which ambient air can enter the system 4000, an exhaust outlet 4016 via which air can be exhausted from the system 4000, and two gas reservoirs in the form of first and second filters 4002, 4004 located between the air inlet 4014 and the exhaust outlet 4016, each filter comprising the selectively sorbent filter material.

In some developments, the system 4000 also includes a moisture filter 4006, located upstream of both the first and second filters 4002, 4004 such that the ambient air entering the system 4000 flows through the moisture filter 4006 before it flows through either of the first or second filters 4002, 4004. The moisture filter 4006 is for removing water molecules from the ambient air, as discussed previously.

The system 4000 further comprises a number of gas feeds 4008 which connect the various components of the system 4000 together so that air can flow between the components through the system 4000.

The system 4000 includes a number of valves 4010, positioned at various locations along the gas feeds 4008 (as has been discussed before in relation to the previous PSA system 2000) in order to control the flow of air through the gas feeds 4008 and into, or out of, the filters 4002, 4004.

A pump 4012, in the form of a vacuum pump, is also connected to the PSA system 4000, using a gas feed 2008, which acts to draw air out of the first and second filters 4002, 4004 by decreasing the pressure in the filters 4002, 4004.

In general, during operation, ambient air is pushed into the system 4000 via the air inlet 4014, passes through the system, in particular the filters 4002, 4004 via the gas feeds 4008, and either exits the system via the exhaust outlet 4016 or via a mixture port 4013.

The filters 4002, 4004 have the same structure, and operate generally in the same manner, as has been described with respect to the carbon dioxide capturing system using PSA and so they will not be described again.

In order to remove the nitrogen from the ambient air, the ambient air is passed through the sorbent material contained within the first filter 4002 under pressure. This can be achieved using a number of different mechanisms.

According to a first mechanism, the ambient air can be drawn through the sorbent filter material using a pump 4011 located upstream of the sorbent material. The pump 4011 forces the ambient air, under pressure, firstly through a valve 4010 and subsequently through the sorbent material in the first filter 4002. The sorbent material captures some of the nitrogen from the ambient air as it passes through the filter 4002. The air which is passed through the filter 4002, as a result of the pressure applied to the system 4000 by the pump 4012, contains a reduced amount of nitrogen gas which is then fed through another valve 4010 into a collection device or the gas mixing device 3. The exhausted air containing reduced nitrogen is then ready to be mixed with carbon dioxide and ambient air as necessary to produce the ventilation gas. For some systems, a restrictor valve can be fitted on the exhaust outlet 4016 to further increase the pressure in the filter PSA system 4000, in order to increase the filter performance.

A second mechanism uses a different pump mechanism, relying on pulling air through the filter system 4000 rather than pushing air through the filter system 4000. Thus, in this case, instead of having a pump located upstream of the sorbent material, the pump 4015 is located downstream of the sorbent material. This pump 4015 draws the ambient air through down a pressure gradient, firstly through a first valve 4010 and subsequently through the sorbent material in the first filter 4002. The sorbent material captures some of the nitrogen as the ambient air passes through the filter 4002 so that the air that passes through the filter comprises a reduced amount of nitrogen compared to the ambient air. Again, this air is then drawn through a second valve 4010 and into a collection device or the gas mixing device 3 where is can be used to produce the ventilation gas mixture.

A final mechanism operates on a similar principle to the second mechanism in that the ambient air is drawn through the filter system 4000 rather than pushed through. However, in this case, instead of using a pump to drawn the air through, the ambient air is drawn through as a result of the user inhaling through the ventilation mask. Thus, in this case, the human lung is performing the function of the pump (that is, applying a suction force to the system to draw the ambient air through the system) and so no pump is required.

The process of capturing and releasing nitrogen by the sorbent material within the filter 4002 is the same as that used in relation to the carbon dioxide PSA system and so will not be described again. In the case of nitrogen removal, Thus the ambient air that has passed through the filter 4002 (i.e. nitrogen reduced air) is then exhausted out of the system 4000 and fed into the gas mixing device 3 via a gas feed 4008. Here, the nitrogen reduced air is then mixed with other gases (such as oxygen, carbon dioxide enhanced air, and ambient air, either individually or in combination) which have been supplied to and entered the gas mixing device 3 via a number of other gas inlets to generate the correct air mixture for ventilation. The ventilation gas mixture is then fed from the gas mixing device 3 into the ventilation mask via another gas feed and a gas mixture outlet 2003.

The nitrogen extracted from the filter 4002 using the vacuum pump 4012 is released to the surroundings as waste gas, via pressure release valve and the exhaust outlet 2016.

As seen in FIG. 17, there are two filters 4002, 4004. In this dual filter system, one filter 4002 is cleaned using a vacuum pump 4011, operatively connected to both the first and second filters 4002, 4004, to remove any remaining gas captured in the sorbent material, while the other filter 4004 is used to adsorb nitrogen from the ambient air and exhaust nitrogen reduced air to the collection device.

The system 4000 alternates the cleaning and filtering functions between the two filters 4002, 4004. Thus, once one of the filters has been cleaned it will switch functions to filtering and removing nitrogen from the ambient air. At the same time, the filter which was performing the nitrogen removal will then switch to being cleaned.

The system 4000 cycles between the two filters by closing and opening a series of valves in the system, in a similar manner to that described previously with reference to FIG. 15. These valves can be electrically or mechanically actuated, controlled by either a fixed mechanical or electrical timer, or be a microprocessor based upon measured oxygen levels from a sensor within the system.

Now, with reference to FIG. 18, an example process of nitrogen removal using TSA will be described. As before, TSA works by passing air through a sorbent material contained within a filter. This process is normally achieved under pressure, i.e. under a pressure which is greater than standard atmospheric pressure, in order to obtain very high oxygen purity. Whilst this system will operate at ambient pressure air, using air at higher pressure improves the system oxygen purity performance. Again, since the aim of the system is to provide carbon dioxide to the mask wearer, only small quantities of nitrogen filtering are required in order to rebalance the ventilation air mixture back to 20.95% oxygen.

The filter material used for nitrogen filtration is generally the same type of filter material that is used for carbon dioxide capture or for nitrogen filtration using PSA i.e. a selectively sorbent filter material being selective towards nitrogen this time rather than carbon dioxide. As before, any suitable selective sorbent material can be used, such as, but not limited to, 13X, or a bespoke manufacture Metal Organic Framework (MOF) material.

The mechanism by which the ambient air is passed through the filter system using TSA is generally the same as the mechanism for passing ambient air through the filtration system using PSA. Thus, the first, second, and final mechanisms for moving ambient air through the filter systems apply to the TSA system and will not be described again.

Figure 18:
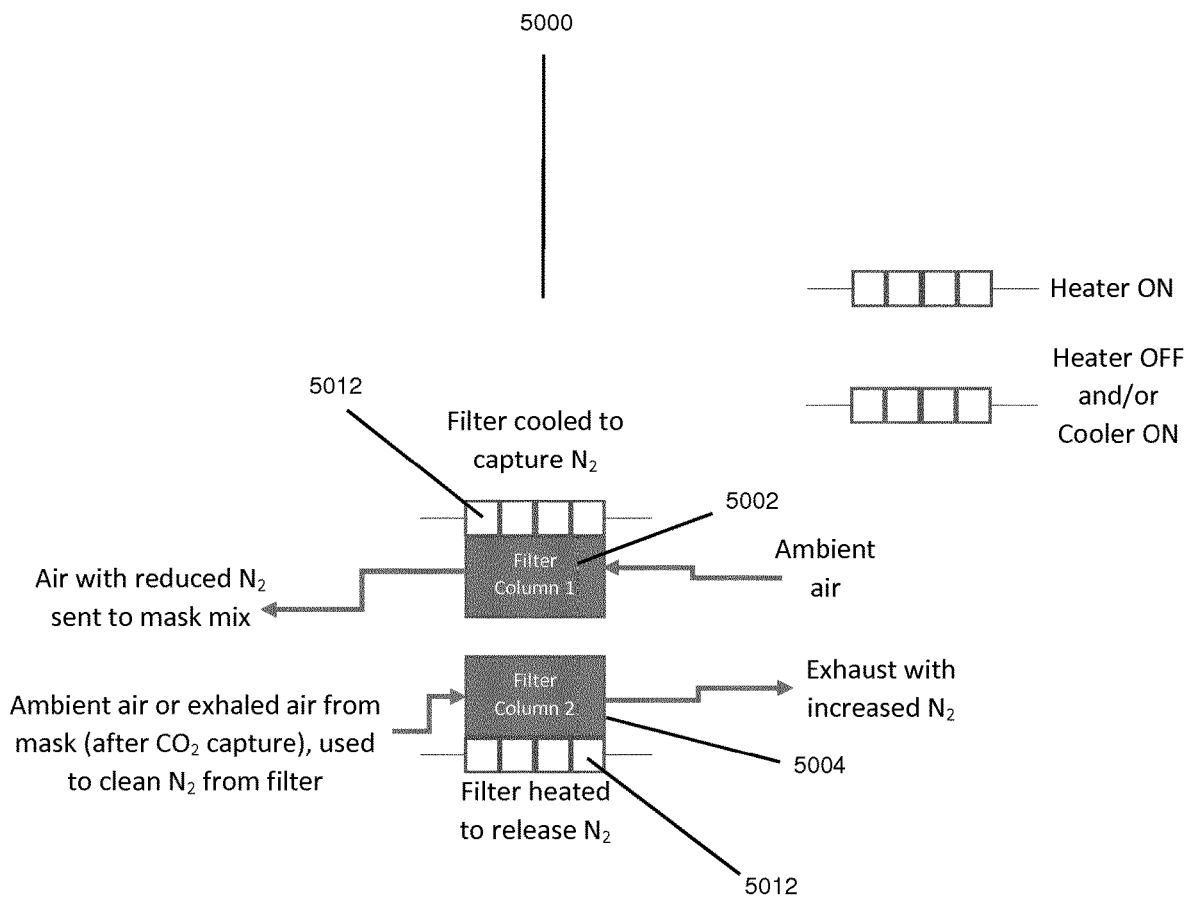
FIG. 18: a schematic representation of a temperature swing adsorption system for nitrogen removal.

Again, FIG. 18 shows an example system in the form of a dual filter system 5000, which has the same configuration as the previously described TSA filter system 3000 and operates in the same way, and so these details will not be described again.

In the dual filter system shown in FIG. 18, one filter 5002 is cleaned using a temperature control means 5012 to heat the filter to remove the nitrogen enhanced air from the filter to be exhausted to the surroundings, while the other filter 5004 is used to adsorb nitrogen from the ambient air as it passes through this other filter 5004, this other filter being in a cooled state as described previously in relation to carbon dioxide capture, and exhaust the nitrogen reduced air to the collection device. The specific temperature associated with the cooled state is particular to the characteristics of each sorbent material and is therefore different depended upon the selected material.

The air which is passes through the capturing filter and exhausted via the exhaust outlet contains a reduced quantity of nitrogen, compared to the ambient air that entered the system, and hence an increased quantity of oxygen, which is then mixed with other gases to generate the correct gas mix to be delivered to the ventilation mask. Once the capturing filter is full or the releasing filter is empty (or based upon either pre-set timing or measured gas properties), a system of valves is used to switch the storage filter into the releasing filter and vice versa, as has been described previously. Again, more than two filters can be used in this configuration where addition filters may be used in series or parallel, or where filters are rested or cooled as part of the cycle. The control can be based upon electrical or mechanical timers, or an electrical or computer-based control system.

As before, the system 5000 alternates the cleaning and filtering functions between the two filters so that once one of the filters has been cleaned it will switch functions to filtering and removing nitrogen from the ambient air. At the same time, the filter which was performing the nitrogen removal will then switch to being cleaned. As described earlier, the system cycles between the two filters by closing and opening a series of valves in the system. These valves can be electrically or mechanically actuated, controlled by either a fixed mechanical or electrical timer, or be a microprocessor based upon measured oxygen levels from a sensor within the system.

The nitrogen reduced air, produced using either PSA or TSA is then passed to the gas mixing device 3 in order to form the ventilation gas mixture. Referring back to FIG. 8, the second reservoir 504' having a filter 5041' allows components from the exhaled air, in this case nitrogen reduced air, to be made available to the second reservoir 504' so that the components can form part of the ventilation gas mixture. The components extracted from the exhaled air are stored in the second reservoir 504', ready for discharge and usage, as required.

As discussed in relation to TSA systems for carbon dioxide capture, heating and cooling of the filters may be achieved by a number of different methods, including, but not limited to refrigerants, Peltiers, electrical coils, and natural cooling or air-cooling. Furthermore, multiple combinations of heating and cooling can be used simultaneously.

Although the PSA nitrogen filtration system 4000 and TSA nitrogen filtration system 5000 have been described separately, in some examples the nitrogen filtration system will use both PSA and TSA. This combination system will include the components from each individual PSA system and TSA system that have been described above. Using a combination of both PSA and TSA to remove nitrogen from ambient air results in a combination system that is more compared to using either PSA or TSA alone.

The skilled person will appreciate that various modifications can be made to the above described systems. For example, in relation to carbon dioxide capture, the exhaled air from the user is exhausted into the cabin air and the carbon dioxide is captured and recycled from this cabin air which includes the exhaled air. However, instead of exhausting the exhaled air into the cabin, the exhaled air could be exhausted into a suitable container, for example a bag, which would temporarily store the exhaled breath. This exhaled air can subsequently be used either fully or partially to be recycled back into the PSA/TSA carbon dioxide capture system.

The sorbent filter design used for carbon dioxide capturing and nitrogen removal in either the PSA or TSA systems can be a packed bed design. However, any other suitable filter design may be used that is able to carry out the required functions to capture and release carbon dioxide or nitrogen from air.

With reference to the TSA system used for both carbon dioxide capture and nitrogen removal, in some cases natural (ambient) cooling, or cooling by means of passing air (which may be pumped, inhaled, or exhaled) through the filter are also possible methods of cooling the TSA filter.

Overall control of either the PSA or TSA system for carbon dioxide capture of nitrogen removal can be achieved using a mechanical timed system which includes at least one timer configured to control the operation of the valves in the system between open and closed systems, which in turn controls the function of the filter between capturing and releasing functions. Alternatively, control may be achieved by a computer control system. This computer control system can be implemented in a number of different ways.

A first implementation uses a digital or analogue electrical control circuit comprising a plurality of sensors that are configured to measure temperature (for example a temperature sensor) and pressure (for example a pressure sensor) of carbon dioxide and oxygen, including the total or partial pressure of an individual gas rather than the combination of gases. The sensors are located at specific points within the system. The sensors can be located external to the filter, i.e. outside the filter housing, or inside the filter and are arranged to measure the temperature and pressure of the ambient air entering and leaving the filter. Typically, an oxygen and/or carbon dioxide partial pressure sensor would typically be located at the inflow and out-flow points of the filter. These sensors are therefore located before and after the filter. Total pressure sensors can be located both within the filter housing and outside the filter at the inflow and outflow points. A temperature sensor may be located within the filter itself to measure the filter temperature, however temperature sensors may also be located at the filter gas in-flow and outflow points.

The control circuit is configured to activate the appropriate control valves, pumps and/or temperature control means in line with pre-determined parameters, conditions or logic. In some cases, the electrical control circuit may comprise additional components for example additional sensors, such as moisture sensors, which are configured to determine any other required measurement to optimise the process.

A second implementation uses a microprocessor, which is configured to receive signals from a plurality of sensors, the sensors configured to measure temperature and pressure of both or either carbon dioxide and oxygen (or the total pressure and temperature). Again, these sensors are located a specific points throughout the system, as described above in relation to the first implementation. The microprocessor is configured to process the received signals and, based upon these processed signals, activate the appropriate control valves, pumps and/or heaters in line with pre-defined parameters, conditions or logic. In some cases, the microprocessor may be configured to receive signals from additional components for example additional sensors, such as moisture sensors, which are configured to determine any other required measurement to optimise the process.

A final implementation uses a mechanical system, such as mechanical timers or barometric capsules, in order to change the state of electrical or mechanical systems. For example the mechanical system may be configured to, but is not limited to, the use of a barometric capsule to activate/deactivate a different number of carbon dioxide TSA modules, dependent upon the altitude, in order to provide variable carbon dioxide levels with altitude.

It should be noted that in some cases there is no active control system. This may be the case in the event that a pre-configured set of system restrictors may allow the system to reach a steady-state condition after a short period of usage and so no further active control is required after this steady state has been reached.

Any of the above described systems can be powered using a range of power sources, including, but not limited to aircraft power, battery power, vehicle power, mains power, or portable power generation (e.g. wind power, solar power, or harnessing the human breath energy via a small turbine).

As the skilled person will understand, there are a number of different configurations in which any of the above described systems could be employed. Some of these configurations, and their corresponding applications, will be outlined below.

Figure 19:
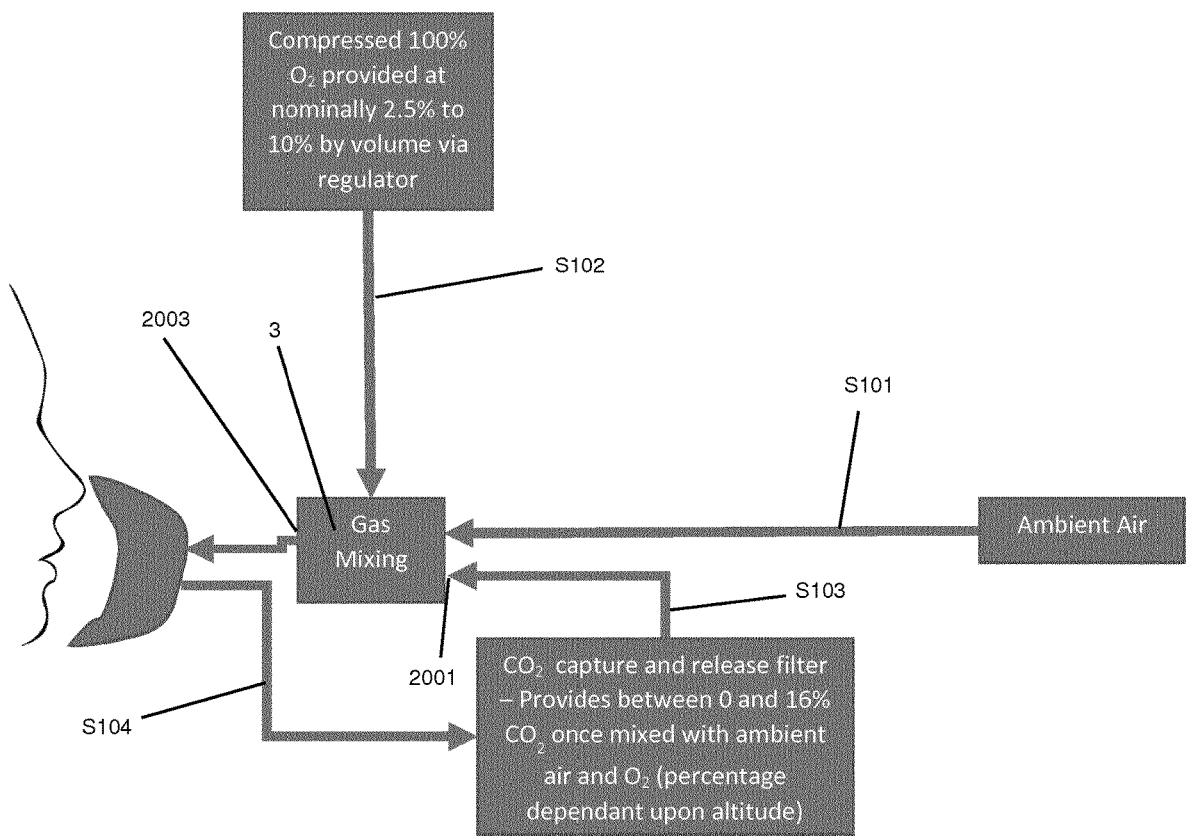
FIG. 19: a ventilation system and mask for use during mountaineering or within an aircraft.

In a first application, shown in FIG. 19, the system may be used in combination with a ventilation mask for providing ventilation gas mixtures for use during mountaineering or for aircraft crew or passengers. This system comprises a gas mixing device 3 in fluid communication with a ventilation mask. The gas mixing device 3 takes in ambient air from the surroundings S101 as well as substantially oxygen S102, which is provided at nominally between 2.5%-10% by volume to the gas mixing device via a regulator. When operating at higher altitudes, the percentage of oxygen can be increased to up to 100%. The oxygen may be supplied from a compressed gas container or chemically generated using a chemical generator, either of which may include a temporary storage reservoir between the generator and the mixer system. The gas mixing device also receives carbon dioxide S103 from a carbon dioxide capture and release filter which is configured to provide a gas mixture having between 0% and 16% carbon dioxide to the ventilation mask, once mixed with the ambient air and oxygen in the gas mixing device. This carbon dioxide capture and release filter could be either the PSA system 2000, the TSA system 3000, a combination of both systems. The actual percentage of carbon dioxide will depend on the altitude. Exhaled air from the user is captured S104 and passed back into the carbon dioxide capture and release filter so that carbon dioxide gas can be captured and reused from this exhaled air. Although the gas mixing device has been shown as separate from the ventilation mask, in some configurations the gas mixing device and filter are part of the ventilation mask, that is to say the gas mixing device and carbon dioxide filter are contained within or attached to the ventilation mask.

Figure 20:
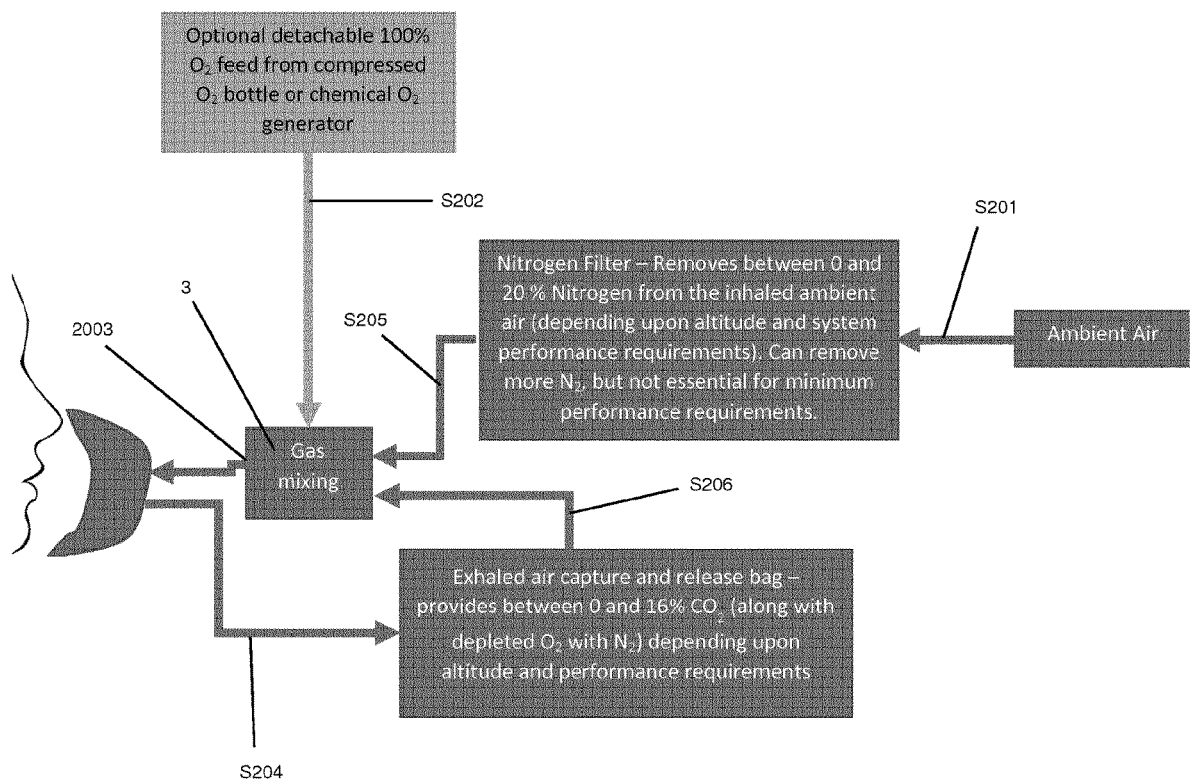
FIG. 20: a ventilation system and mask for use during mountaineering or within an aircraft.

In a second application, shown in FIG. 20, the system may be used in combination with a ventilation mask to provide ventilation gas mixtures for use during mountaineering or for aircraft passengers or crew. This system comprises a gas mixing device in fluid communication with a ventilation mask. The gas mixing device 3 takes in ambient air from the surroundings S201, the ambient air firstly being passed through a nitrogen filter S205 to form nitrogen reduced air before entering the gas mixing device. This nitrogen filter could be either the PSA system 4000, the TSA system 4000, a combination of both systems. The nitrogen filter is configured to remove between 0% and 20% nitrogen from the ambient air, depending on the altitude. In some cases, more than 20% nitrogen could be removed. The gas mixing device may also optionally take in oxygen S202, which is provided to the gas mixing device via either a compressed oxygen container or a chemical oxygen generator, either of which may include a temporary storage reservoir between the generator and the mixer system. As well as being optional, the system can work such that it is connected to 100% oxygen for the initial emergency descent, e.g. from 40,000 ft to nominally 21,000 ft, and then this oxygen supply line can be detached to allow free movement around the cabin, e.g. at nominally 21,000 ft.

The gas mixing device also receives carbon dioxide S206 from a carbon dioxide storage container, for example an exhaled air capture and release bag, which is configured to capture and store exhaled air from a person. In this application, the exhaled air is not passed through a carbon dioxide capture filter. Instead, the exhaled air within the storage container is then mixed with the nitrogen reduced air from the nitrogen filter (and/or the oxygen from the chemical generator or bottle). The carbon dioxide storage container is configured to provide exhaled air having between 0% and 16% carbon dioxide to the gas mixing device. The nominal resultant air mix sent to the mask for a 21,000 ft case, would be 21% oxygen (or higher), 12% carbon dioxide, and the remaining volume as nitrogen and other gasses. The actual percentage of carbon dioxide will depend on the altitude. Again, exhaled air from the user is captured and passed back into the gas mixing device so that carbon dioxide gas can be captured and reused from this exhaled air. Although the gas mixing device has been shown as separate from the ventilation mask and filters, in some configurations the gas mixing device and filters are part of the ventilation mask.

Figure 21:
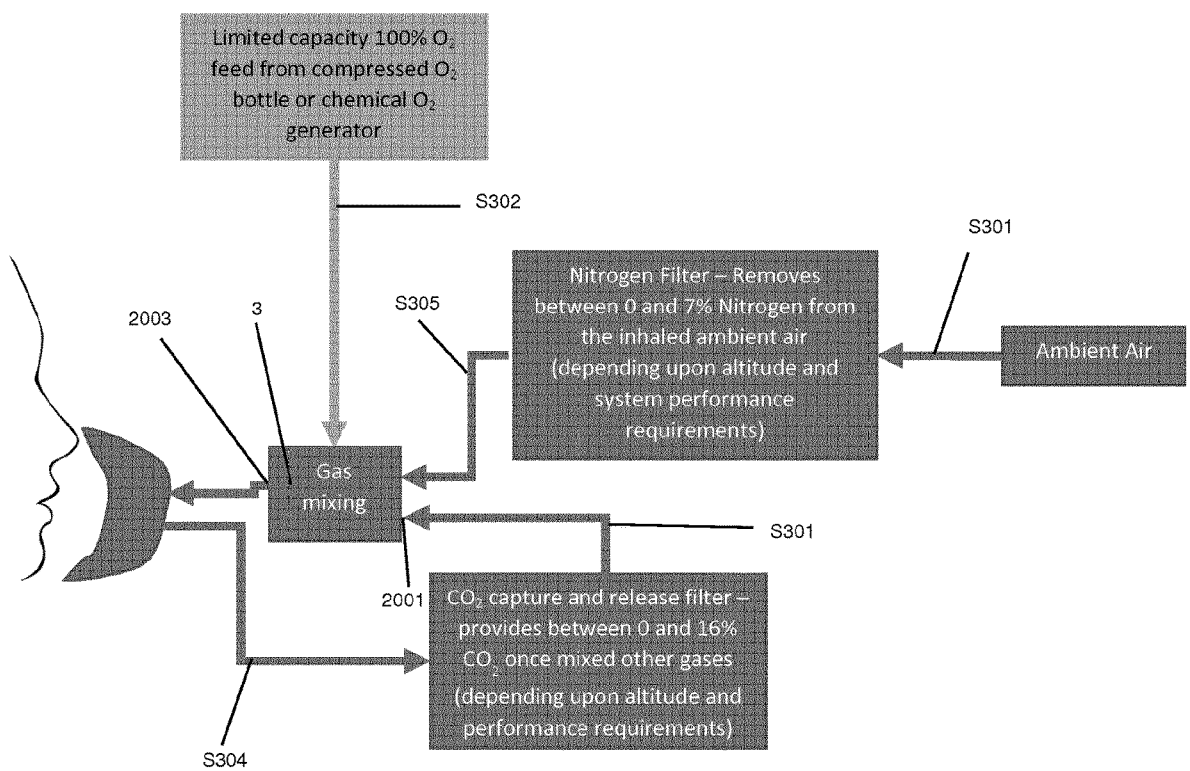
FIG. 21: a ventilation system and mask for use within aircraft.

In a third application, shown in FIG. 21, the system may be used in combination with a ventilation mask to provide ventilation gas mixtures for aircraft crew or passengers. This system comprises a gas mixing device 3 in fluid communication with a ventilation mask. The gas mixing device 3 takes in ambient air from the surroundings S301, the ambient air firstly being passed through a nitrogen filter S305 to form nitrogen reduced air before entering the gas mixing device. This nitrogen filter could be either the PSA system 4000, the TSA system 4000, a combination of both systems. The nitrogen filter is configured to remove between 0% and 7% nitrogen from the ambient air, depending on the altitude. The gas mixing device is also connected to a limited capacity oxygen feed which is arranged to provide oxygen S302 to the gas mixing device via a compressed oxygen container or a chemical oxygen generator. This oxygen supply may be optional, or only provided temporarily. For example, the system can work such that it is connected to oxygen for the initial emergency descent, e.g. from 40,000 ft to nominally 21,000 ft, and then this oxygen supply line can be detached to allow free movement around the cabin, e.g. at nominally 21,000 ft.

The gas mixing device also receives S301 carbon dioxide from a carbon dioxide capture and release filter which is configured to provide a gas mixture having between 0% and 16% carbon dioxide to the ventilation mask, once mixed with the nitrogen reduced ambient air and optionally the oxygen in the gas mixing device. This carbon dioxide capture and release filter could be either the PSA system 2000, the TSA system 3000, a combination of both systems. The nominal resultant air mix sent to the mask for a 21,000 ft case, would be 21% oxygen (or higher), 12% carbon dioxide and the remaining volume as nitrogen and other gasses. The actual percentage of carbon dioxide will depend on the altitude. Exhaled air from the user is captured and passed back S304 into the carbon dioxide capture and release filter so that carbon dioxide gas can be captured and reused from this exhaled air. Although the gas mixing device has been shown as separate from the ventilation mask and filters, in some configurations the gas mixing device and filters are part of the ventilation mask.

The invention claimed is:

1. An apparatus for preparing a ventilation gas mixture that comprises:
   a gas mixing device;
   a first gas feed arranged to supply a first gas to the gas mixing device;
   an air inlet configured to receive exhaled air from a person;
   a combination carbon dioxide capturing system comprising a carbon dioxide pressure swing absorption system and a carbon dioxide temperature swing absorption system, wherein the combination carbon dioxide capturing system comprises:
      a first gas reservoir arranged to store carbon dioxide from the air received in the air inlet and further arranged to supply the stored carbon dioxide to the gas mixing device via a second gas feed; and
   a combination nitrogen capturing system comprising a nitrogen pressure swing absorption system and a nitrogen temperature swing absorption system, wherein the combination nitrogen capturing system comprises:
   a second gas reservoir arranged to receive ambient air via a second gas reservoir inlet and further arranged to supply nitrogen reduced ambient air to the gas mixing device;
   wherein the gas mixing device is arranged to combine the first gas with the carbon dioxide in order to prepare the ventilation gas mixture.

2. The apparatus according to claim 1 wherein the first gas reservoir comprises a selectively sorbent material.

3. The apparatus according to claim 2 wherein the sorbent material selectively stores carbon dioxide.

4. The apparatus according to claim 1 wherein the carbon dioxide pressure swing absorption system comprises a pump arranged to apply a pressure to the first gas reservoir relative to surroundings of the first gas reservoir in order to controllably store carbon dioxide within the first gas reservoir or controllably release the carbon dioxide from the first gas reservoir.

5. The apparatus according to claim 4 wherein the pump is arranged to apply a positive pressure to the first gas reservoir in order to store carbon dioxide.

6. The apparatus according to claim 4 wherein the pump is arranged to apply a negative pressure to the first gas reservoir in order to release the carbon dioxide.

7. The apparatus according to claim 1 further comprising a moisture filter arranged to filter the air received from the air inlet before it is supplied to the first gas reservoir.

8. The apparatus according to claim 7 wherein the moisture filter is positioned in a flow path between the air inlet and the first gas reservoir.

9. The apparatus according to claim 1 wherein the combination carbon dioxide capturing system comprises a plurality of first gas reservoirs.

10. The apparatus according to claim 9 wherein each of the plurality of first gas reservoirs is arranged to store carbon dioxide from air received in the air inlet and further arranged to supply the stored carbon dioxide to the gas mixing device.

11. The apparatus according to claim 10 wherein a primary gas reservoir in the plurality of first gas reservoirs is configured to carry out a capturing function in which the primary gas reservoir is configured to store carbon dioxide from air received in the air inlet while a secondary gas reservoir in the plurality of first gas reservoirs is configured to carry out a supplying function in which the secondary gas reservoir is configured to supply stored carbon dioxide to the gas mixing device.

12. The apparatus according to claim 11 further comprising one or more valves associated with the plurality of first gas reservoirs, the one or more valves arranged to switch the function of the primary gas reservoir to the supplying function and the function of the secondary gas reservoir to the capturing function.

13. The apparatus according to claim 9 wherein the plurality of first gas reservoirs are fluidly coupled together via a common gas feed.

14. The apparatus according to claim 9 wherein the plurality of first gas reservoirs are coupled together in series.

15. The apparatus according to claim 9 wherein the plurality of first gas reservoirs are coupled together in parallel.

16. The apparatus according to claim 1 wherein the carbon dioxide temperature swing capturing system comprises a temperature control means arranged to adjust the temperature of the first gas reservoir in order to controllably store carbon dioxide within the first gas reservoir or controllably release the carbon dioxide from the first gas reservoir.

17. The apparatus according to claim 16 wherein the temperature control means is arranged to decrease the temperature of the first gas reservoir in order to controllably store carbon dioxide within the first gas reservoir.

18. The apparatus according to claim 16 wherein the temperature control means is arranged to increase the temperature of the first gas reservoir in order to controllably release carbon dioxide from the first gas reservoir.

19. The apparatus according to claim 1 wherein the second gas reservoir comprises a selectively sorbent material.

20. The apparatus according to claim 19 wherein the sorbent material selectively stores nitrogen.

21. The apparatus according to claim 1 wherein the nitrogen temperature swing absorption system comprises a temperature control means arranged to adjust the temperature of the second gas reservoir in order to controllably store nitrogen within the second gas reservoir or controllably release the nitrogen from the second gas reservoir.

22. The apparatus according to claim 21 wherein the temperature control means is arranged to decrease the temperature of the second gas reservoir in order to controllably store nitrogen within the second gas reservoir.

23. The apparatus according to claim 21 wherein the temperature control means is arranged to increase the temperature of the second gas reservoir in order to controllably release nitrogen from the second gas reservoir.

24. The apparatus according to claim 1 wherein the nitrogen pressure swing absorption system comprises a pump arranged to apply a pressure to the second gas reservoir relative to surroundings of the second gas reservoir in order to controllably store nitrogen within the second gas reservoir or controllably release the nitrogen from the second gas reservoir.

25. The apparatus according to claim 24 wherein the pump is arranged to apply a positive pressure to the second gas reservoir in order to store nitrogen.

26. The apparatus according to claim 24 wherein the pump is arranged to apply a negative pressure to the second gas reservoir in order to release the nitrogen.

27. The apparatus according to claim 1 further comprising a ventilation mask configured to receive the ventilation gas mixture from the gas mixing device.

28. The apparatus according to claim 27 wherein the first gas reservoir forms part of the ventilation mask.

29. The apparatus according to claim 27 wherein the second gas reservoir forms part of the ventilation mask.

30. The apparatus according to claim 1 further comprising an intermediate reservoir located between the air inlet and the first gas reservoir and/or the second gas reservoir, configured to store air received from the air inlet.

31. The apparatus according to claim 1 wherein the ventilation gas mixture comprises at least 15% v/v oxygen, 0%-16% v/v carbon dioxide, and nitrogen.

32. A ventilation mask configured to supply a ventilation gas mixture to a person, the ventilation mask comprising:
a gas mixing device comprising an air outlet;
a first gas feed arranged to supply a first gas to the gas mixing device;
a combination carbon dioxide capturing system comprising a carbon dioxide pressure swing absorption system and a carbon dioxide temperature swing absorption system, wherein the combination carbon dioxide capturing system comprises:
a first gas reservoir comprising an air inlet arranged to receive exhaled air from a person and to store carbon dioxide from the air received via the air inlet, the first gas reservoir further arranged to supply the stored carbon dioxide to the gas mixing device via a second gas feed; and
a combination nitrogen capturing system comprising both a nitrogen pressure swing absorption system and a nitrogen temperature swing absorption system, wherein the combination nitrogen capturing system comprises:
a second gas reservoir arranged to receive ambient air via a second gas reservoir inlet and further arranged to supply nitrogen reduced ambient air to the gas mixing device;
wherein the gas mixing device is arranged to combine the first gas with the carbon dioxide in order to prepare the ventilation gas mixture, the gas mixing device further arranged to supply the ventilation gas mixture to a person via the air outlet.

33. A method of preparing a ventilation gas mixture comprising the steps of:
supplying a first gas to a gas mixing device via a first gas feed;
receiving exhaled air from a person via an air inlet;
supplying the air received from the air inlet to a first gas reservoir within a combination carbon dioxide capturing system comprising a carbon dioxide pressure swing absorption system and a carbon dioxide temperature swing absorption system;
storing carbon dioxide from the air exhaled by a person in the first gas reservoir;
supplying the stored second gas to the gas mixing device via a second gas feed; and
receiving ambient air in a second gas reservoir via a second gas reservoir inlet, wherein the second gas reservoir is within a combination nitrogen capturing system comprising a nitrogen pressure swing absorption system and a nitrogen temperature swing absorption system;
supplying nitrogen reduced ambient air to the gas mixing device;
wherein the gas mixing device combines the first gas with the carbon dioxide in order to prepare the ventilation gas mixture.

34. The method according to claim 33 wherein the ventilation gas mixture comprises at least 15% v/v oxygen and 0%-16% v/v carbon dioxide.

35. The method according to claim 33 further comprising delivering the ventilation gas mixture to a person via a ventilation mask.

36. The method according to claim 35 wherein the ventilation mask comprises:
the gas mixing device comprising an air outlet;
the first gas feed arranged to supply the first gas to the gas mixing device;
the combination carbon dioxide capturing system comprising the carbon dioxide pressure swing absorption system and the carbon dioxide temperature swing absorption system, wherein the combination carbon dioxide capturing system comprises:
the first gas reservoir comprising the air inlet arranged to receive exhaled air from a person and to store carbon dioxide from the air received via the air inlet, the first gas reservoir further arranged to supply the stored carbon dioxide to the gas mixing device via the second gas feed; and
the combination nitrogen capturing system comprising the nitrogen pressure swing absorption system and the nitrogen temperature swing absorption system, wherein the combination nitrogen capturing system comprises:
the second gas reservoir arranged to receive ambient air via the second gas reservoir inlet and further arranged to supply nitrogen reduced ambient air to the gas mixing device;
wherein the gas mixing device is arranged to combine the first gas with the carbon dioxide in order to prepare the ventilation gas mixture, the gas mixing device further arranged to supply the ventilation gas mixture to a person via the air outlet.

* * * * *